United States Patent
Chronis et al.

(10) Patent No.: US 12,376,835 B2
(45) Date of Patent: Aug. 5, 2025

(54) LIQUID ACTIVATED DEVICES AND SYSTEMS

(71) Applicant: THE REGENTS OF THE UNIVERSITY OF MICHIGAN, Ann Arbor, MI (US)

(72) Inventors: Nikolaos Chronis, Ann Arbor, MI (US); Petros Papagerakis, Saskatoon (CA); Silvana Papagerakis, Saskatoon (CA); Amrita Ray Chaudhury, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 1237 days.

(21) Appl. No.: 16/971,985

(22) PCT Filed: Feb. 21, 2019

(86) PCT No.: PCT/US2019/018966
§ 371 (c)(1),
(2) Date: Aug. 21, 2020

(87) PCT Pub. No.: WO2019/165078
PCT Pub. Date: Aug. 29, 2019

(65) Prior Publication Data
US 2020/0397416 A1    Dec. 24, 2020

Related U.S. Application Data

(60) Provisional application No. 62/633,963, filed on Feb. 22, 2018.

(51) Int. Cl.
*A61B 10/00* (2006.01)

(52) U.S. Cl.
CPC .... *A61B 10/0051* (2013.01); *A61B 2010/009* (2013.01)

(58) Field of Classification Search
CPC .. A61B 10/0045–0051; A61B 10/0058; A61B 10/0064; A61B 10/007;
(Continued)

(56) References Cited

U.S. PATENT DOCUMENTS

| 4,595,011 A | 6/1986 | Phillips |
| 5,167,626 A * | 12/1992 | Casper ............... A61B 10/0045 600/582 |

(Continued)

FOREIGN PATENT DOCUMENTS

| WO | WO-2005046485 A1 * | 5/2005 | ......... A61B 10/0045 |
| WO | WO 2016/044338 | 3/2016 | |

OTHER PUBLICATIONS

International Search Report and Written Opinion for PCT/US19/18966. Mailed May 14, 2019. 14 pages.
(Continued)

*Primary Examiner* — Alex M Valvis
*Assistant Examiner* — Jonathan E. Cooper
(74) *Attorney, Agent, or Firm* — Casimir Jones, S.C.; Jason R. Bond

(57) ABSTRACT

The present invention relates to systems, devices, kits, and methods employing liquid activated devices and systems. In certain embodiments, the liquid activated devices comprise a base substrate and a chamber sealing system (CSS) and/or a sealed reservoir system (SRS). In some embodiments, the CSS is sealed inside the reservoir of the SRS by a liquid degradable membrane. In particular embodiments, a liquid (e.g., saliva) un-seals the reservoir exposing the CSS, which
(Continued)

seals the micro-chamber therein upon exposure to the liquid (e.g., trapping some of the liquid in the micro-chamber for analysis).

18 Claims, 12 Drawing Sheets

(58) Field of Classification Search
CPC .... A61B 2010/0054; A61B 2010/0058; A61B 2010/0061; A61B 2010/0067; A61B 2010/0074; A61B 2010/0077; A61B 2010/008; A61B 5/682; A61B 10/0051; A61C 7/36; A61F 5/566
USPC ........................................................ 600/582
See application file for complete search history.

(56) References Cited

U.S. PATENT DOCUMENTS

| | | | |
|---|---|---|---|
| 5,352,803 | A | 10/1994 | Mattingly |
| 5,359,093 | A | 10/1994 | Adamczyk et al. |
| 5,496,925 | A | 3/1996 | Mattingly |
| 5,573,904 | A | 11/1996 | Mattingly |
| 5,593,896 | A | 1/1997 | Adamczyk et al. |
| 8,551,016 | B2 | 10/2013 | Slowey et al. |
| 2004/0267159 | A1 | 12/2004 | Yong et al. |
| 2007/0106138 | A1 | 5/2007 | Beiski et al. |
| 2007/0255177 | A1* | 11/2007 | Pronovost .......... A61B 10/0051 600/573 |
| 2008/0194912 | A1* | 8/2008 | Trovato ................ A61B 34/72 600/118 |
| 2009/0012503 | A1* | 1/2009 | Kawano ................ F04B 43/06 604/891.1 |
| 2009/0216082 | A1* | 8/2009 | Rabinovitz ........ A61B 10/0045 600/118 |
| 2012/0123297 | A1* | 5/2012 | Brancazio ........ A61B 5/150022 600/576 |
| 2014/0212986 | A1 | 7/2014 | Angelescu et al. |
| 2014/0350473 | A1 | 11/2014 | Lee et al. |
| 2016/0331356 | A1 | 11/2016 | Binner et al. |
| 2017/0343566 | A1* | 11/2017 | Burgess ............. A61B 10/0051 |
| 2018/0368961 | A1* | 12/2018 | Shanjani ............. A61B 5/4547 |
| 2019/0099129 | A1* | 4/2019 | Kopelman ............. A61B 5/682 |

OTHER PUBLICATIONS

Adamczyk et al., Chemiluminescence quenching of pteroic acid-N-sulfonyl-acridinium-9-carboxamide conjugates by folate binding protein. Bioorg Med Chem Lett May 3, 2004;14(9):2313-7.
Adamczyk et al., Chemiluminescent acridinium-9-carboxamide boronic acid probes: application to a homogeneous glycated hemoglobin assay. Bioorg Med Chem Lett. Mar. 1, 2006;16(5):1324-8.
Adamczyk et al., Intrinsic factor-mediated modulation of cyanocobalamin-N-sulfonyl-acridinium-9-carboxamide chemiluminescence. Bioorg Med Chem Lett. Aug. 2, 2004;14(15):3917-21.
Adamczyk et al., Regiodependent luminescence quenching of biotinylated N-sulfonyl-acridinium-9-carboxamides by avidin. Org Lett. Oct. 16, 2003;5(21):3779-82.
Au et al., Microvalves and Micropumps for BioMEMS. Micromachines 2011, 2(2), 179-220.
Benloucif et al., Measuring melatonin in humans. J Clin Sleep Med. Feb. 15, 2008;4(1):66-9.
Bjorvatn et al., A practical approach to circadian rhythm sleep disorders. Sleep Med Rev. Feb. 2009;13(1):47-60.
Burgess et al., Home Circadian Phase Assessments with Measures of Compliance Yield Accurate Dim Light Melatonin Onsets. Sleep. Jun. 1, 2015;38(6):889-97.
Burgess et al., Individual Differences in the Amount and Timing of Salivary Melatonin Secretion. PLoS One. 2008, 3(8), 9 pages.
Castagnola et al., Salivary biomarkers and proteomics: future diagnostic and clinical utilities. Acta Otorhinolaryngol Ital. Apr. 2017;37(2):94-101.
Dang et al., Morphological Characterization of Polyanhydride Biodegradable Implant Gliadel® During in Vitro and in Vivo Erosion Using Scanning Electron Microscopy. Pharmaceutical Research, 1996, 13, 683-691.
Frost and Sullivan: US and European Sleep Disorder Diagnostic Devices Market Cost-effective Solutions in Home Sleep Tests Stir Market Growth, M9AC-54 Feb. 2014. Retrieved from the internet Sep. 8, 2023. 4 pages.
Grassl et al., Ultra-deep and quantitative saliva proteome reveals dynamics of the oral microbiome. Genome Med. Apr. 21, 2016;8(1):44.
Haugland, Handbook of Fluorescent Probes and Research Chemicals. Molecular Probes. 1996. TOC only. 4 pages.
Keijzer et al., Why the dim light melatonin onset (DLMO) should be measured before treatment of patients with circadian rhythm sleep disorders. Sleep Med Rev. Aug. 2014;18(4):333-9.
Khurshid et al., Human Saliva Collection Devices for Proteomics: An Update. Int J Mol Sci. 2016, 17(6): 846. 1-10.
Klerman et al., Comparisons of the variability of three markers of the human circadian pacemaker. J Biol Rhythms. Apr. 2002;17(2):181-93.
Kotzar et al., Evaluation of MEMS materials of construction for implantable medical devices. Biomaterials 2002, 23, 2737-2750.
Lewy et al., The circadian basis of winter depression. Proc Natl Acad Sci U S A. May 9, 2006;103(19):7414-9.
Lewy et al., The endogenous melatonin profile as a marker for circadian phase position. J Biol Rhythms. Jun. 1999;14(3):227-36.
Lockley. Timed Melatonin Treatment for Delayed Sleep Phase Syndrome: The Importance of Knowing Circadian Phase. Sleep, 2005, vol. 28, No. 10. 1214-1216.
Millet et al., Characterization of Mass and Swelling of Hydrogel Microstructures using MEMS Resonant Mass Sensor Arrays. Hydrogel Microsturctures. 2012 8 pages.
Oh et al., A review of microvalves. J. Micromech. Microeng. 2006, 16: R13-R39.
Polak et al., Introduction to Immunocytochemistry, 2nd ed., Springer Verlag, N.Y. 1997. TOC only. 10 pages.
SalivaBio, SalivaBio's Saliva Colleciton Aid Receives Patent Approval. Retrieved from the internet Jun. 2, 2023. https://salimetrics.com. 2 pages.
Sateia. International Classification of Sleep Disorders, third edition. Chest, 2014, 146(5), 1387-1394.
Whitaker-Brothers et al., Investigation into the erosion mechanism of salicylate-based poly(anhydride-esters). Journal of Biomedical Materials Research Part A, 2006, 76A(3), 470-479.

* cited by examiner

FIG. 1A-B

FIG. 3A-B
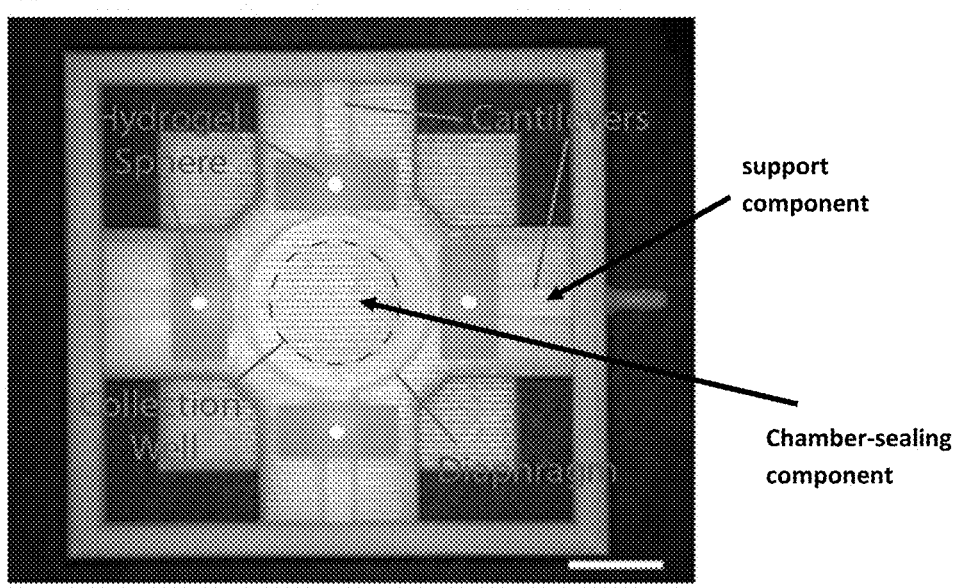
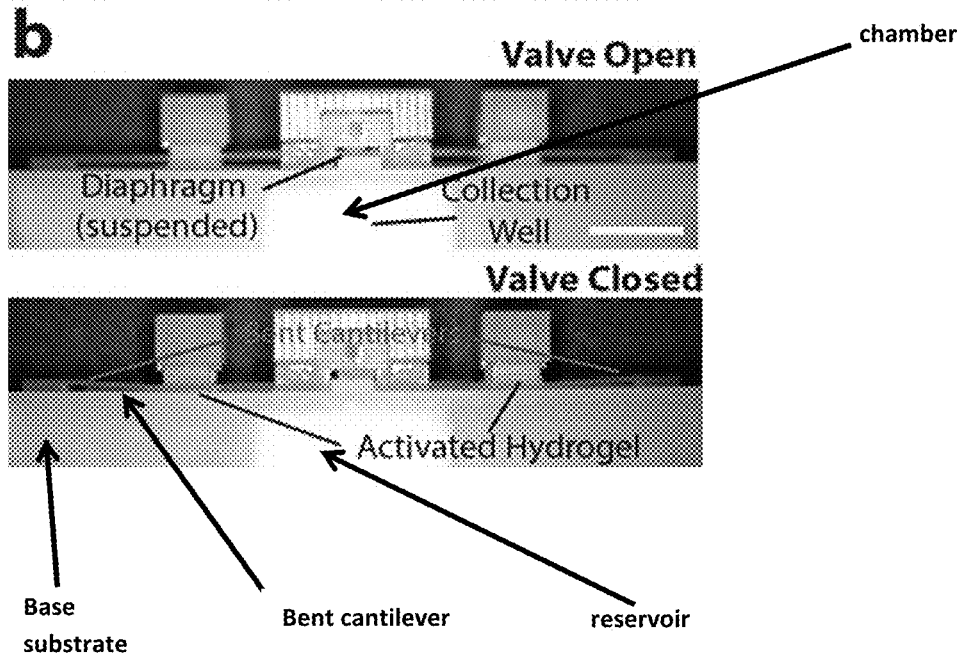

LIQUID ACTIVATED DEVICES AND SYSTEMS

The present application is a § 371 National Entry application of PCT/US2019/018966, filed Feb. 21, 2019, which claims priority to U.S. Provisional application 62/633,963, filed Feb. 22, 2018, each of which are herein incorporated by reference in its entirety.

FIELD OF THE INVENTION

The present invention relates to systems, devices, kits, and methods employing liquid or electrically activated devices and systems. In certain embodiments, the devices comprise a base substrate and a chamber sealing system (CSS) and/or a sealed reservoir system (SRS). In some embodiments, the CSS is sealed inside the reservoir of the SRS by a liquid degradable membrane. In particular embodiments, a liquid (e.g., saliva) un-seals the reservoir exposing the CSS, which seals the micro-chamber therein upon exposure to the liquid (e.g., trapping some of the liquid in the micro-chamber for analysis).

BACKGROUND

Sleep disorders are among the most common clinical problems encountered in medicine and psychiatry. Inadequate or nonrestorative sleep can markedly impair a patient's quality of life. Americans are notoriously sleep deprived, but those with psychiatric conditions are even more likely to be yawning or groggy during the day. Chronic sleep problems affect 50%-80% of patients in a typical psychiatric practice, compared with 10%-18% of adults in the general U.S. population. Sleep problems are particularly common in patients with anxiety, depression, bipolar disorder, and attention deficit hyperactivity disorder. Traditionally, clinicians treating patients with psychiatric disorders have viewed insomnia and other sleep disorders as symptoms. However, recent studies in adults and children suggest that sleep problems may raise risk for, and even directly contribute to, the development of psychiatric disorders but also to other chronic conditions including cardiovascular diseases, diabetes, obesity, etc. Although melatonin is a key biomarker for diagnosis of sleep disorders, no widely applied protocols exist to systematically measure melatonin expression.

Sleep disorders result from an endogenous disturbance in sleep-wake generating or timing mechanisms orchestrated by the circadian clock systems. In humans, the most reliable measure of central circadian timing is the onset of melatonin secretion, when measured in dim light conditions (dim light melatonin onset, DLMO). Melatonin typically begins to rise in the 2-3 h before the usual onset of nocturnal sleep, but must be measured in dim light because light can suppress melatonin secretion. The measurement of the DLMO is now established among the diagnostic criteria for circadian rhythm sleep disorders. Additionally, measuring the DLMO can help to optimize the treatment of circadian rhythm sleep disorders with melatonin or bright light and help to prevent patients from receiving treatment at the wrong circadian time, which risks worsening their condition. Similarly, measuring the DLMO or "phase typing" patients with winter depression can assist in optimizing the timing of bright light treatment. Although melatonin is established as a diagnostic and prognostic marker for sleep disorders, it is only used for selected patients due to the complexity of the current protocol that requires 24 hour stay in specialized clinics and excellent patience compliance (who are requested to spit and collect saliva every 30-60 min for 24 hrs).

Saliva sampling is reliable method for field, clinical, and research trials, provided that samples are taken every 30 to 60 minutes under dim light (<30 lux) for at least 1 hour prior to and throughout the expected rise in melatonin. The collection requires hospitalization and also that the subjects remain in dim light and follow instructions to avoid contamination of samples with food particles, food dye, or blood. Young children and older adults may require extra monitoring or assistance to ensure compliance with the protocol and to obtain a sufficient quantity of sample for analysis. Furthermore, the constant disruption or complete deprivation of sleep that occurs during frequent salivary sample collection limits its use. Therefore, DLMO measurement although very important for diagnosis and treatment remains unutilized for the majority of sleep disorder patients that may benefit of it. Accordingly, there is a significant unmet need for accurate assessment of circadian phase outside of the clinic/laboratory, particularly with the gold standard dim light melatonin onset (DLMO).

SUMMARY OF THE INVENTION

The present invention relates to systems, devices, kits, and methods employing liquid activated devices and systems. In certain embodiments, the liquid activated devices comprise a base substrate and a chamber sealing system (CSS) and/or a sealed reservoir system (SRS). In some embodiments, the CSS is sealed inside the reservoir of the SRS by a liquid degradable membrane. In particular embodiments, a liquid (e.g., saliva) un-seals the reservoir exposing the CSS, which seals the micro-chamber therein upon exposure to the liquid (e.g., trapping some of the liquid in the micro-chamber for analysis).

In some embodiments, provided herein are liquid activated devices comprising: a) a base substrate (e.g., retainer, mouthpiece, intra-oral device, water testing device, plastic support, etc.), and b) at least one of the following liquid activated systems attached to, or integral with, the base substrate: i) at least one chamber sealing system comprising: A) a chamber, B) a chamber-sealing component, and C) at least one support component attached to the chamber-sealing component, wherein the at least one support component holds the chamber-sealing component at least partially away from the chamber such that the chamber is not sealed, wherein the at least one support component comprises liquid-activated material, and wherein the at least one support components is configured to change shape and/or size when contacted by a liquid causing the chamber-sealing component to seal the chamber; and ii) at least one sealed reservoir system comprising: A) a reservoir, B) at least one reservoir component inside the reservoir, wherein the reservoir component is selected from the group consisting of: a sample detection component (e.g., melatonin detection reagents or water quality detection reagents), a sample collection component (e.g., a chamber sealing system described herein), and a therapeutic agent component (e.g., a pre-sealed microchamber that contains a therapeutic agent; or a therapeutic agent that is in the reservoir but not in a microchamber), and C) a liquid degradable membrane stretching across the reservoir such that the at least one reservoir component is sealed inside the reservoir.

In some embodiments, provided herein are liquid activated device comprising: a) a base substrate, and b) at least one of the following liquid activated systems attached to, or integral with, said base substrate: i) at least one chamber sealing system comprising: A) a chamber, B) a chamber-sealing component, and C) at least one support component attached to said chamber-sealing component, wherein said at least one support component: i) holds said chamber-sealing component at least partially away from said chamber such that said chamber is not sealed, or ii) holds said chamber-sealing component against said chamber such that said chamber is sealed, wherein said at least one support component comprises liquid-activated material, and wherein said at least one support components is configured to change shape when contacted by a liquid causing: i) said chamber-sealing component to seal said chamber if initially not sealed, or ii) said chamber-sealing component to un-seal said chamber if initially sealed; and ii) at least one sealed reservoir system comprising: A) a reservoir, B) at least one reservoir component inside said reservoir, wherein said reservoir component is selected from the group consisting of: a sample detection component, a sample collection component, and a therapeutic agent component, and C) a liquid degradable membrane stretching across said reservoir such that said at least one reservoir component is sealed inside said reservoir.

In certain embodiments, the at least one support component holds said chamber-sealing component at least partially away from said chamber such that said chamber is not sealed and said at least one support components is configured to change shape when contacted by a liquid causing said chamber-sealing component to seal said chamber. In particular embodiments, the at least one support component holds said chamber-sealing component against said chamber such that said chamber is sealed, and said at least one support components is configured to change shape when contacted by a liquid causing said chamber-sealing component to un-seal said chamber. In some embodiments, the un-sealing of said chamber releases a therapeutic or other agent from said chamber.

In certain embodiments, provided herein are chamber sealing or un-sealing systems comprising: a) a chamber, b) a chamber-sealing component, and c) at least one support component attached to said chamber-sealing component, wherein said at least one support component: i) holds said chamber-sealing component at least partially away from said chamber such that said chamber is not sealed, or ii) holds said chamber-sealing component against said chamber such that said chamber is sealed, wherein said at least one support component comprise liquid-activated material, and wherein said at least one support component is configured to change shape when contacted by a liquid causing: i) said chamber-sealing component to seal said chamber if initially not sealed, or ii) said chamber-sealing component to un-seal said chamber if initially sealed.

In some embodiments, provided herein are methods comprising: a) placing a liquid activated device described herein, a chamber sealing or un-sealing system as described herein, a sealed reservoir system as described herein, or a liquid capture system described herein, in a location for a time period such that at least one of said liquid activated systems is exposed to liquid; and b) removing said liquid activated device, said chamber sealing/un-sealing system, and/or said sealed reservoir system, from said location.

In certain embodiments, the sample collection component comprises the at least one chamber sealing system. In other embodiments, the base substrate comprises an intra-oral device. In further embodiments, the intra-oral device comprises at least part of a mouthpiece, retainer, oral appliance, or oral orthotic. In other embodiments, the base substrate comprises a waterway sampling device. In certain embodiments, the liquid is selected from: saliva, rain water, pond water, lake water, river water, ocean water, drinking water treatment plant water, sewage-treatment plant water, urine, blood, plasma, serum, or other biological sample. In particular embodiments, at least one liquid activated system comprises at least one of the chamber sealing systems and at least one of the sealed reservoir systems (e.g., where the camber sealing system is located inside the seated reservoir system).

In further embodiments, the at least one sealed reservoir system comprises: i) a first sealed reservoir system with a first liquid degradable membrane and a first reservoir, and ii) a second sealed reservoir system with a second liquid degradable membrane and a second reservoir; wherein the first and second aqueous sample degradable membranes have a different thicknesses and/or are composed of different materials that degrade at different rates. In certain embodiments, the at least one sealed reservoir system comprises second, third, fourth, fifth . . . twenty-fourth . . . $100^{th}$ . . . or more sealed reservoir systems with second, third, fourth, fifth . . . twenty-fourth . . . $100^{th}$ . . . or more liquid degradable membranes and second, third, fourth, fifth . . . twenty-fourth . . . $100^{th}$ . . . or more reservoirs, all with the same or different (or mixture of same and different) thicknesses of the liquid degradable membrane, and/or are composed of different materials that degrade at different rates. In certain embodiments, the difference in thicknesses, or composition of the membranes, are configured to un-seal the first and second reservoirs at different times when the first and second sealed reservoir systems are exposed to a liquid at the same time. In some embodiments, the thicknesses of the membranes are the same or about the same, and the reservoirs are un-sealed at, or about, the same time when exposed to liquid.

In some embodiments, the chamber has a liquid volume of between 1 and 75 µl (e.g., 1 . . . 10 . . . 30 . . . 50 . . . 65 . . . and 75 µl). In particular embodiments, the chamber-sealing component comprises a diaphragm, film, or plastic fitted cover (e.g., snap-fit cover). In other embodiments, the at least one support component comprises at least two (e.g., 2 . . . 4 . . . 10 . . . or more) cantilevers and at least two hydrogel spheres (e.g., 2 . . . 4 . . . 10 . . . or more). In further embodiments, the at least one support components comprise at least four support components. In additional embodiments, the liquid activated material comprises water-swelling type material. In some embodiments, the reservoir has a volume of between 20 µl and 600 µl (e.g., 20 . . . 30 . . . 100 . . . 350 . . . 500 . . . or 600 µl).

In certain embodiments, the at least one reservoir component is the sample detection component. In further embodiments, the sample detection component comprises at least of the following: an analyte binding component, an analyte activated component, a detectable label, a secondary label, and components of a nucleic acid detection assay, and components of a protein detection assay. In other embodiments, the analyte binding component is selected from the group consisting of: an anti-analyte antibody or analyte binding portion thereof, a nucleic acid sequence configured to hybridize to the analyte, a small molecule configured to bind to the analyte, an aptamer for the analyte, and a receptor for the analyte. In certain embodiments, the analyte is melatonin or an analyte described in Castagnola et al. (Acta Otorhin. Italica, 2017, 37:94-101, which is herein incorporated by reference in its entirety as if fully set forth herein, particularly with respect to the biomarker analytes describe therein). In certain embodiments, the analyte detected is a microorganism. Examples of such microorganisms in saliva that may be detected are found in Grassl et al., Genome Med., 2016, 8:44, which is herein incorporated by reference, as if fully set forth herein, particularly with respect to the microorganisms present in saliva described therein, including the 50 bacterial genera described in FIG. 4). In certain embodiments, the liquid degradable membrane comprises polyanhydride. In certain embodiment, the analyte is a bacteria, virus, fungi, microorganisms, or particular DNA, RNA, protein, or peptide.

In other embodiments, provided herein are chamber sealing systems comprising: a) a chamber (e.g., micro-chamber), b) a chamber-sealing component, and c) at least one support component attached to the chamber-sealing component, wherein the at least one support components hold the chamber-sealing component at least partially away from the chamber such that the chamber is not sealed, wherein the at least one support component comprise liquid-activated material, and wherein the at least one support components is configured to change shape when contacted by a liquid causing the chamber-sealing component to seal the chamber. In certain embodiments, the systems further comprising the liquid, wherein the liquid is selected from the group consisting of: rain water, pond water, lake water, river water, ocean water, drinking water treatment plant water, and sewage-treatment plant water.

In other embodiments, provided herein are sealed reservoir systems comprising: a) a reservoir, b) at least one reservoir component inside the reservoir, wherein the reservoir component is selected from the group consisting of: a sample detection component, a sample collection component, and a therapeutic agent component (e.g., a pre-sealed microchamber that contains a therapeutic agent; or a therapeutic agent that is in the reservoir but not in a microchamber), and c) a liquid degradable membrane stretching across the reservoir such that the at least one reservoir component is sealed inside the reservoir. In particular embodiments, the systems further comprise the liquid, wherein the liquid is selected from the group consisting of: rain water, pond water, lake water, river water, ocean water, drinking water treatment plant water, and sewage-treatment plant water.

In some embodiments, provided herein are methods comprising: placing the liquid activated devices described above and herein, a chamber sealing system described above and herein, or a sealed reservoir system described above and herein, in a location such that at least one of the liquid activated systems is exposed to liquid.

In certain embodiments, provided herein are methods comprising: a) placing the liquid activated devices described above and herein, a chamber sealing system described above and herein, and/or sealed reservoir system described above and herein, in a location for a time period such that at least one of the liquid activated systems is exposed to liquid; and b) removing the liquid activated device, the chamber sealing system, and/or the sealed reservoir system, from the location.

In some embodiments, provided herein are liquid capture systems comprising: a) a reservoir, b) a chamber located inside the reservoir, c) a moveable stage that stretches across the reservoir such that the chamber is sealed inside the reservoir, wherein the moveable stage comprises: i) a cover component that is sized to seal the reservoir when contacting the reservoir, and seal the chamber when contacting the chamber, ii) liquid-activated material configured to change shape when contacted by liquid, d) at least two support components attached to the cover component, wherein the at least two support components hold the cover component in a first position that seals the reservoir, but does not seal the chamber, when the liquid activated material is not yet exposed to liquid, and wherein the at least two support components hold the cover component in a second position that does not seal the reservoir, but does seal the chamber, when the liquid activated material has been exposed to liquid.

In certain embodiments, the moveable stage further comprises a substrate with liquid openings which is located over the top of the liquid activated material. In other embodiments, the at least two support components comprise at least two cantilever-type springs. In additional embodiments, the liquid activated material comprises a hydrogel bead or other expanding material.

In certain embodiments, the location is an oral cavity of a subject. In other embodiments, the location is in a body of water. In other embodiments, the body of water is selected from a pond, lake, river, estuary, ocean, creek, and tidal pool. In further embodiments, the location is an outdoor plot of land exposed to rainfall or snow. In additional embodiments, the liquid degradable membrane of the sealed reservoir system is partially or completely degraded during the time period at the location after being exposed to the liquid. In certain embodiments, the methods are employed to monitor sleep patterns, athletic performance, veterinary health, pregnancy status, ovulation status, viral infection levels, inflammation levels, biological indicators of mood disorders, indicators of autoimmune diseases, antibodies, DNAs, RNAs, peptides, micro-organisms (e.g., viruses), toxins, radiation, glucose level, blood alcohol levels, diet impact on health, bacterial levels, melatonin levels, pH levels, cancer biomarkers, to monitor results of clinical trial, or to monitor particular biomarker levels (e.g., single time point or multi-time points are monitored over time). In some embodiments, the biomarker is from a particular subject, such as an athlete, soldier, person with sleep disorder, etc. In certain embodiments, the methods and devices are used to monitor various marker and other levels in nocturnal animals and other animals. In some embodiments, one or more biomarkers is detected after a physiological activity, such as before or after exercise, during or after trauma, before, during or after sleep, or after an intervention such as diet, light therapy, etc.

In other embodiments, the at least one support component of the chamber sealing system changes shape after being exposed to the liquid during the time period at the location causing the chamber-sealing component to seal the chamber. In other embodiments, a portion of the liquid is sealed in the chamber. In further embodiments, after the removing step, at portion of liquid in the sealed chamber is analyzed to determine the presence and/or concentration of at least one analyte. In further embodiments, the portion of the liquid is removed from the sealed chamber prior being analyzed. In other embodiments, the portion of liquid remains in the chamber when it is analyzed.

In some embodiments, provided herein are electrically activated devices comprising: a) a base substrate, and b) at least one of the following electrically activated systems attached to, or integral with, said base substrate: i) at least one chamber sealing system comprising: A) a chamber, B) a chamber-sealing component, and C) at least one support component attached to said chamber-sealing component, wherein said at least one support component: i) holds said chamber-sealing component at least partially away from said chamber such that said chamber is not sealed, or ii) holds said chamber-sealing component against said chamber such that said chamber is sealed, wherein said at least one support component comprises thermally expanding material and electrically conductive material, and wherein said at least one support components is configured to change shape when activated by electrical current causing: i) said chamber-sealing component to seal said chamber if initially not sealed, or ii) said chamber-sealing component to un-seal said chamber if initially sealed; and ii) at least one sealed reservoir system comprising: A) a reservoir, B) at least one reservoir component inside said reservoir, wherein said reservoir component is selected from the group consisting of: a sample detection component, a sample collection component, and a therapeutic agent component, and C) a liquid degradable membrane stretching across said reservoir such that said at least one reservoir component is sealed inside said reservoir. In certain embodiments, the thermally expanding material comprises a thermally expanding polymer. In other embodiments, the electrically conductive heats up electrical current passes therethrough.

In some embodiments, provided herein are chamber sealing or un-sealing systems comprising: a) a chamber, b) a chamber-sealing component, and c) at least one support component attached to said chamber-sealing component, wherein said at least one support component: i) holds said chamber-sealing component at least partially away from said chamber such that said chamber is not sealed, or ii) holds said chamber-sealing component against said chamber such that said chamber is sealed, wherein said at least one support component comprises thermally expanding material and electrically conductive material, wherein said at least one support components is configured to change shape when activated by electrical current causing: i) said chamber-sealing component to seal said chamber if initially not sealed, or ii) said chamber-sealing component to un-seal said chamber if initially sealed.

BRIEF DESCRIPTION OF THE FIGURES

FIG. 1 panel A, left side, further shows that a plurality of the MRUs attached with a base substrate (e.g., mouthpiece) such that an array of MRUs are present in a single liquid activated device. FIG. 1, panel B also shows an array of MRUs with three separate MRUs, each with a degradable membrane with a different thickness.

FIG. 3, panel A shows an exemplary 3D printed saliva container (top view) described in Example 1. FIG. 3, panel B shows results of exposing the hydrogel sphere to liquid such that such sphere push cantilevers and diaphragm to seal the micro-chamber. The top picture in FIG. 3B shows prior to liquid exposure and the bottom picture shows after liquid exposure.

FIG. 5, right side, shows the components of a chamber sealing system (which may be inside the sealed reservoir system), as described in Example 2.

FIG. 7a (bottom left) shows that the biomorph springs can be passively activated when liquid causes the swellable material to swell, which causes the microchamber to close. FIG. 7b (bottom right) shows that the biomorph spring can be actively activated by electronic control. Electrically conductive material causes the thermally expanding polymer to swell, thereby pushing down and causing the microchamber to be sealed.

DEFINITIONS

The terms "individual," "host," "subject," and "patient" are used interchangeably herein, and generally refer to a mammal, including, but not limited to, primates, including simians and humans, equines (e.g., horses), canines (e.g., dogs), felines, various domesticated livestock (e.g., ungulates, such as swine, pigs, goats, sheep, and the like), as well as domesticated pets and animals maintained in zoos. In some embodiments, the subject is specifically a human subject.

DETAILED DESCRIPTION OF THE INVENTION

The present invention relates to systems, devices, kits, and methods employing liquid activated devices and systems. In certain embodiments, the liquid activated devices comprise a base substrate and a chamber sealing system (CSS) and/or a sealed reservoir system (SRS). In some embodiments, the CSS is sealed inside the reservoir of the SRS by a liquid degradable membrane. In particular embodiments, a liquid (e.g., saliva) un-seals the reservoir exposing the CSS, which seals the micro-chamber therein upon exposure to the liquid (e.g., trapping some of the liquid in the micro-chamber for analysis).

I. Sealed Reservoir Systems

Figure 5:
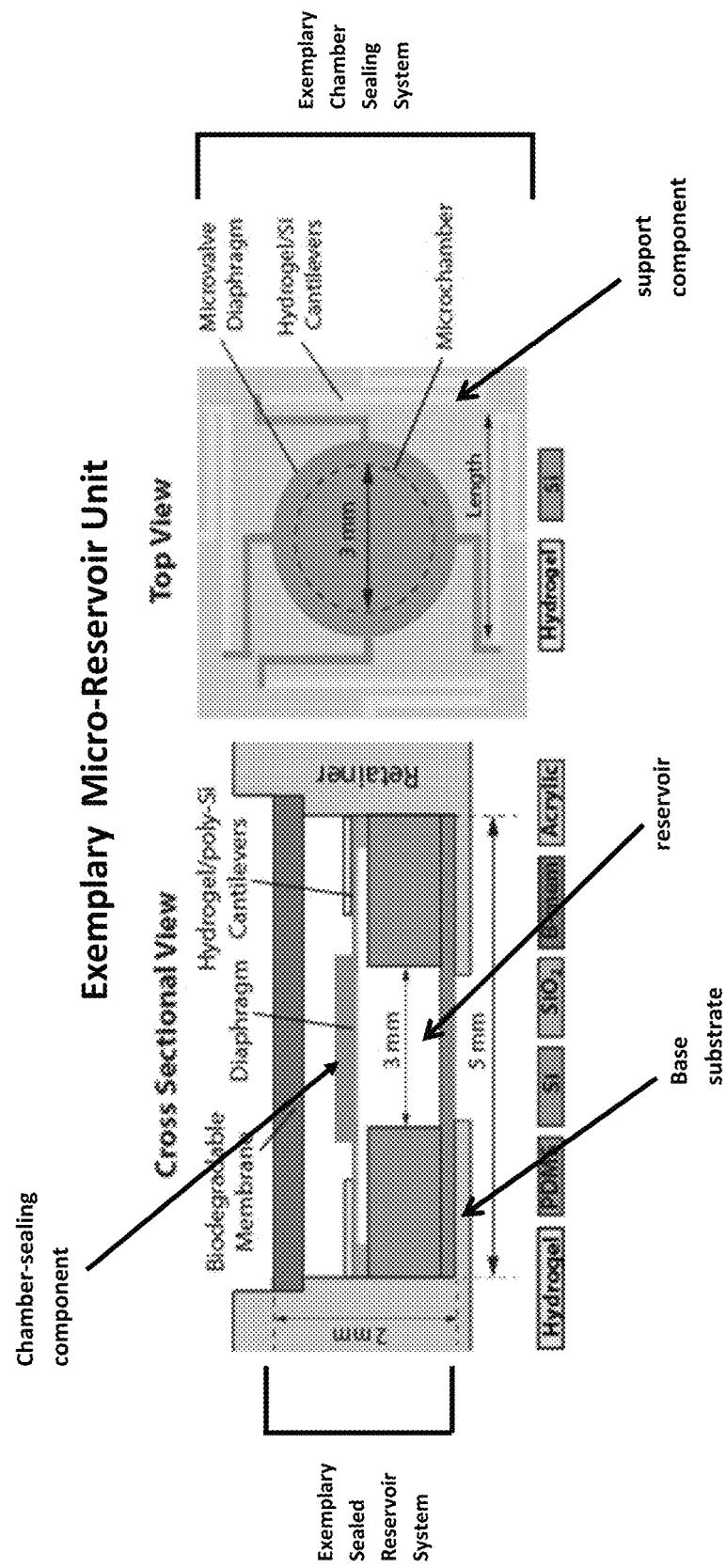
FIG. 5, left side, shows the components of a sealed reservoir system as described in Example 2.
Figure 6A:
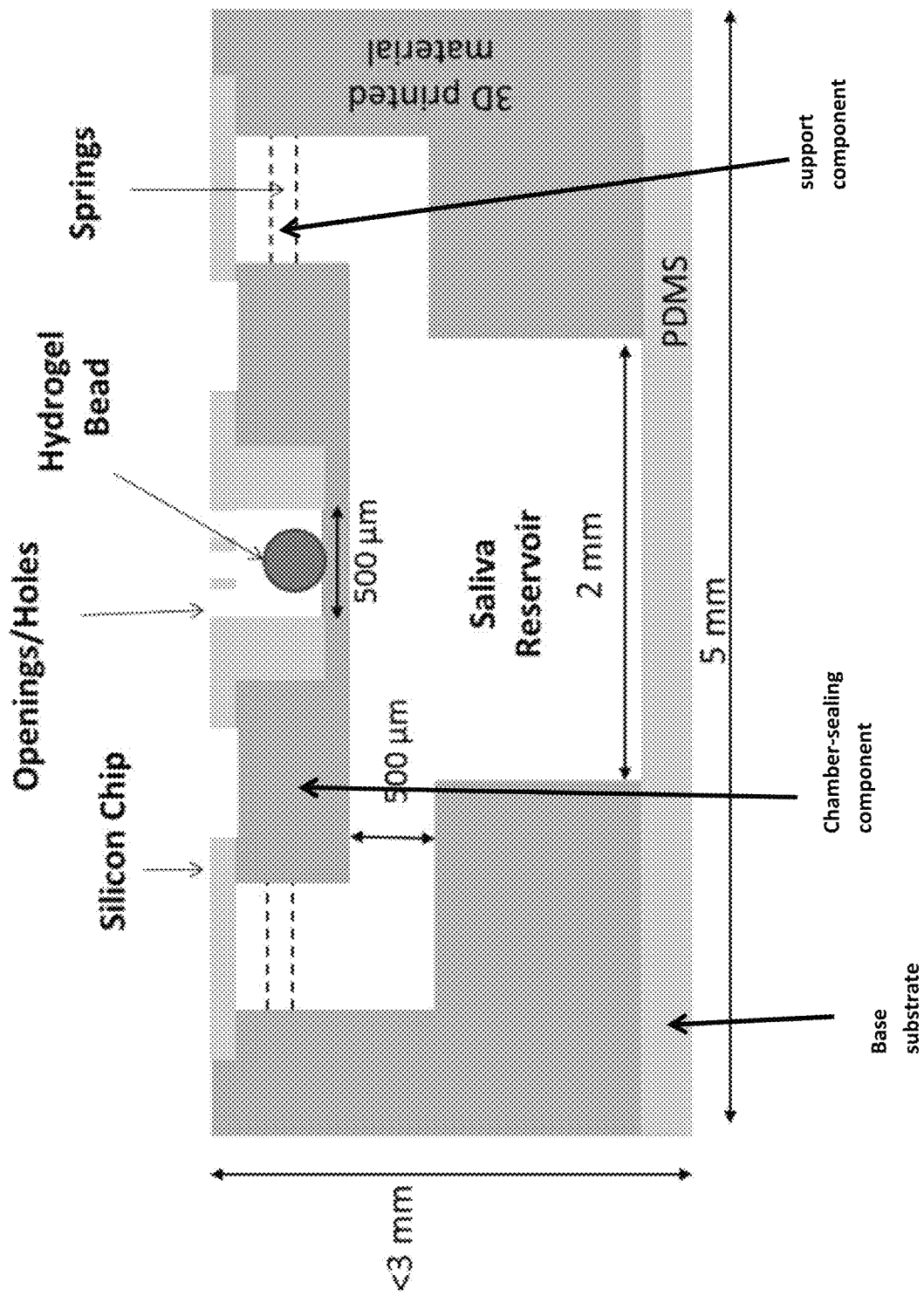
FIG. 6A-C show an exemplary liquid (e.g., saliva) collection device which incorporates a vertically moving stage attached to cantilever-type springs (shown with the dotted lines). The stage houses a hydrogel bead or other swellable material with the same or different shape. A substrate, such as a silicon chip is attached on top of the stage. The silicon chip has openings (e.g. holes) in its center that allow the hydrogel bead to swell/expand when exposed to saliva. The operation of this exemplary device is shown in FIG. 6A (initial position), FIG. 6B (intermediate position) and FIG. 6[C (final position). When the bead is exposed to liquid, it pushes the stage to move downward resulting in the liquid to flow through the openings to the saliva reservoir. As the bead keeps swelling, the stage keeps moving downward and finally after the liquid has been collected in the reservoir, the stage closes/seals the reservoir. In general, the timing of the opening/closing of the device depends on the swelling rate of the swellable material (e.g., hydrogel bead) and on the various design parameters (e.g. dimensions of the chamber that houses the bead).
Figure 6B:
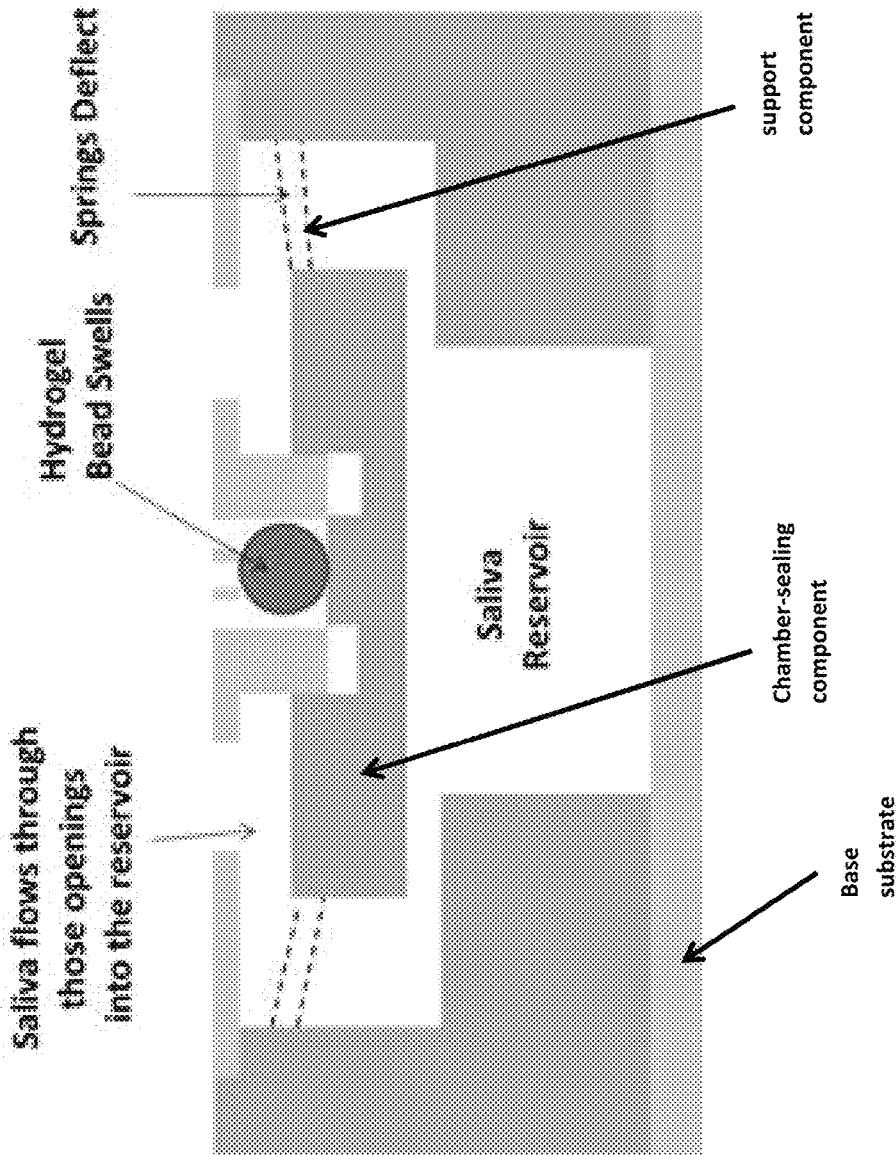
Figure 6C:
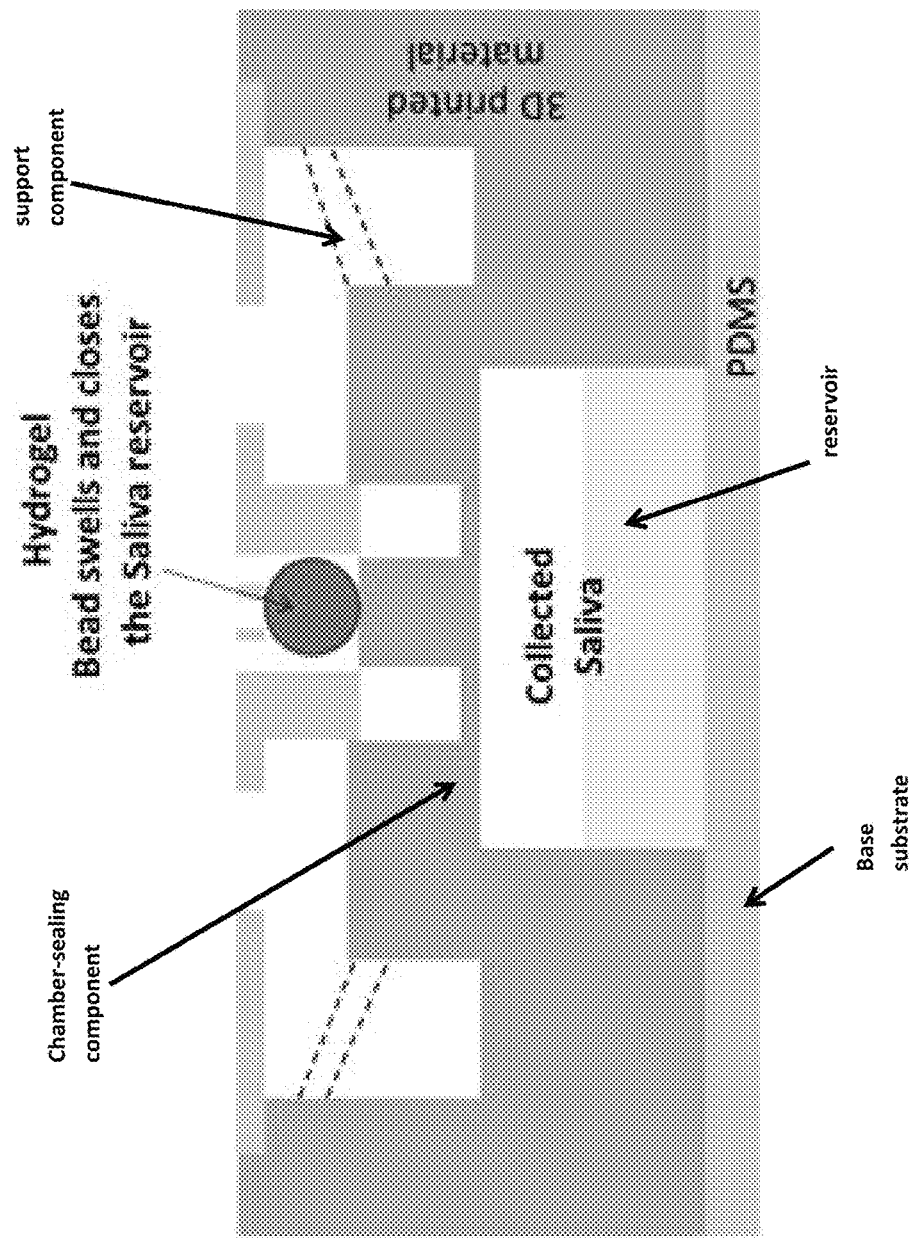

In certain embodiments, provided herein are sealed reservoir systems composed of a reservoir, at least one reservoir component in the reservoir, and a liquid degradable membrane that seals the reservoir component in the reservoir. The reservoir component may any component, such as a sample detection component, a sample collection component, or a therapeutic agent component (e.g., a pre-sealed microchamber that contains a therapeutic agent; or a therapeutic agent that is in the reservoir but not in a microchamber). An exemplary sealed reservoir system is shown in FIG. 5, left side, which shows a chamber sealing system as the reservoir component that is sealed inside the reservoir by the degradable membrane. In particular embodiments, the sealed reservoir system is attached to a base substrate, such as a mouth piece, with indentations created by individual teeth. In certain embodiments, the sealed reservoir system is at the bottom of one of these indentations (see, e.g., FIG. 1). In other embodiments, the sealed reservoir system is next to one of the indentations (e.g., part of a bump-out that does not line up with any teeth indentations).

The liquid degradable membrane may be composed of any useful material that will both seal the underlying reservoir and degrade over time when exposed to a liquid. Examples of such materials include, but are not limited to: a material comprising a polyanhydride, a mixture of poly (ethyleneglycol) (PEG) and polyanhydride, Bio-Gide, Resolut, Vicryl, and OsseoQuest membrane. In certain embodiments, the liquid degradable membranes are composed of polymers selected from: polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(amino acids), polyvinylpyrrolidone, polyethylene glycol, polyhydroxycellulose, chitin, chitosan, and copolymers, terpolymers, or combinations or mixtures of the above materials. The liquid degradable material is not limited to a particular shape, as long as it covers and seals the reservoir.

In certain embodiments, the reservoir contains a sample detection component. The sample detection component may be configured to detect an analyte of interest, including, but not limited to, a small molecule, microorganism, protein, antibody, or particular cell type. In certain embodiments, the sample detection component is configured as a biosensor that quantifies the concentration of small (e.g., 100-300 Da) molecules that are found in low concentrations (<1 nM) in biological fluids, such as saliva. In certain embodiments, the targeted analyte is melatonin in saliva (e.g., for the purpose of ascertaining the timing of an individual's circadian rhythm for precisely scheduling circadian entrainment treatments). In certain embodiments, the biological fluid is blood, plasma, urine, dental plaque, feces, vagina fluid, sperm, nasal or lung secretions. In some embodiments, a subject's breath is captured and tested. In particular embodiments, sample detection component may comprise reagents for conducting a detection assay (e.g., antibody based, nucleic acid based, etc.). In certain embodiments, well-known enzyme chemistry techniques for analytic quantification are integrated the sealed reservoir systems to enhance the sensitivity of the device. In certain embodiments, a probe/piston design is employed for the analytic detection head with each of the enzyme chemistry steps located in their own chamber. In particular embodiments, an electroactive assay is employed. In particular embodiments, electrical and optical components are employed for end-signal detection and requisite analysis (e.g., via a window in the bottom of the reservoir). In certain embodiments, the window in the bottom of the reservoir is piercable such that liquid (e.g., saliva) can be withdrawn, or such that any assay components that are separated by a film may be pierced (e.g., to activate an assay). In certain embodiments, the window and/or film separating chambers is configured to be penetrated by a lollipop probe. In particular embodiments, the bottom of the device (e.g., bottom of reservoir or chamber) is removable, allowing liquid (e.g., saliva) to be collected.

In certain embodiments, biomarkers found in saliva are detected. Examples of such biomarkers are found in Castagnola et al. (Acta Otorhin. Italica, 2017, 37:94-101, which is herein incorporated by reference in its entirety as if fully set forth herein, particularly with respect to the biomarker analytes describe therein). In certain embodiments, specific molecular patterns are detected, such as those relevant to intelligence, surveillance, and reconnaissance (ISR). In other embodiments, the analytes detected drugs or agents of bioterrorism in a waterway or pond. In certain embodiments, the biomarker is employed to detect cancer, such as oral squamous cell carcinoma (OSCC). For example, the biomarker may be: IL-6, IL-8, IL-1$\beta$, cyclin D1 thioredoxin, profiling 1, thrombospondin-2, S100A8, alpha-1-antitrypsin, haptoglobin $\beta$ chains, complement C3, haemopexi, and transthyretin. In certain embodiments, the analyte or biomarker is selected from: phenylalanione, valine, n-eicosanoid acid, lactic acid, gamma-aminobutyric acid, propionylcholine, N-acetyl-L-phenylalanine, sphinganine, phytosphingosine, S-carboxymethyl-L-cystein, alpha-2-macroglobulin, ceruloplamin, cystatin B, triose-phosphate isomerase, T$\beta$4, T$\beta$10, and 'deleted in malignant tumor 1 protein.' In some embodiments, mRNA presence or expression levels are detected (e.g., mRNA to CCNI, EGFR, FGF19, FRS2, and GREB1).

In certain embodiments, the sample detection component employs all or most of the components of a detection assay (e.g., in dried down format). In certain embodiments, the detection assays employ covalent attachment of bioactive proteins (e.g., Melatonin Antibody or a Melatonin Receptor unit) in a layer suitable for capturing small-molecule analytes in saliva. In particular embodiments, the assay components comprise small molecule competitor units composed of the binding group (e.g., Melatonin), an oligomer/spacer, and a signaling enzyme (e.g., a peroxidase or other enzyme capable of creating a signal). In particular embodiments, the detection assays include, but are not limited to: 1) a sandwich immunoassay (e.g., monoclonal, polyclonal and/or DVD-Ig sandwich immunoassays or any variation thereof (e.g., monoclonal/DVD-Ig or DVD-Ig/polyclonal), including chemiluminescence detection, radioisotope detection (e.g., radioimmunoassay (RIA)) and enzyme detection (e.g., enzyme immunoassay (EIA) or enzyme-linked immunosorbent assay (ELISA) (e.g., Quantikine ELISA assays, R&D Systems, Minneapolis, Minn.))), 2) a competitive inhibition immunoassay (e.g., forward and reverse), 3) a fluorescence polarization immunoassay (FPIA), 4) an enzyme multiplied immunoassay technique (EMIT), 5) a bioluminescence resonance energy transfer (BRET), 6) a homogeneous chemiluminescent assay, 7) a SELDI-based immunoassay, 8) chemiluminescent microparticle immunoassay (CMIA) and 9) a clinical chemistry colorimetric assay (e.g., IMA, creatinine for eGFR determination and LC-MS/MS). (See, e.g., Tietz Textbook of Clinical Chemistry and Molecular Diagnostics. 4th Edition, edited by C A Burtis, E R Ashwood and D E Bruns, Elsevier Saunders, St. Louis, Mo., 2006).

Further, if an immunoassay is being utilized, any suitable detectable label as is known in the art can be used. For example, the detectable label can be a radioactive label (such as 3H, 125I, 35S, 14C, 32P, and 33P), an enzymatic label (such as horseradish peroxidase, alkaline peroxidase, glucose 6-phosphate dehydrogenase, and the like), a chemiluminescent label (such as acridinium esters, thioesters, or sulfonamides; luminol, isoluminol, phenanthridinium esters, and the like), a fluorescent label (such as fluorescein (e.g., 5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, and the like)), rhodamine, phycobiliproteins, R-phycoerythrin, quantum dots (e.g., zinc sulfide-capped cadmium selenide), a thermometric label, or an immuno-polymerase chain reaction label. An introduction to labels, labeling procedures and detection of labels is found in Polak and Van Noorden, Introduction to Immunocytochemistry, 2nd ed., Springer Verlag, N.Y. (1997), and in Haugland, Handbook of Fluorescent Probes and Research Chemicals (1996), which is a combined handbook and catalogue published by Molecular Probes, Inc., Eugene, Oreg. A fluorescent label can be used in FPIA (see, e.g., U.S. Pat. Nos. 5,593,896, 5,573,904, 5,496,925, 5,359,093, and 5,352,803, which are hereby incorporated by reference in their entireties). An acridinium compound can be used as a detectable label in a homogeneous or heterogeneous chemiluminescent assay (see, e.g., Adamczyk et al., Bioorg. Med. Chem. Lett. 16: 1324-1328 (2006); Adamczyk et al., Bioorg. Med. Chem. Lett. 4: 2313-2317 (2004); Adamczyk et al., Biorg. Med. Chem. Lett. 14: 3917-3921 (2004); and Adamczyk et al., Org. Lett. 5: 3779-3782 (2003)).

In particular embodiments, the reservoir component comprises a therapeutic agent component inside the reservoir (e.g., in liquid, solid, or powder form). In some embodiments, the therapeutic agent component comprises one or more therapeutic agents (e.g., useful for treating a disease or condition in a subject). In certain embodiments, the therapeutic agent component comprises a pre-sealed microchamber that contains a therapeutic agent. In particular embodiments, once the liquid degradable membrane is at least partially degraded, one or more therapeutic agents move out of the reservoir and into the oral cavity or other part of a subject. In other embodiments, the therapeutic agent is contained in a pre-sealed microchamber within the reservoir and saliva or other liquid caused the microchamber to become unsealed (or electronics cause the microchamber to become unsealed), releasing the therapeutic agent. In certain embodiments, the therapeutic agent is selected from: a salivation enhancing agent, a salivation inhibiting agent, an anti-cancer agent, a saliva replacement agent (e.g., for people suffering from xerostomia) a dental treatment agent (e.g., anti-plaque agent), and anti-microbial agent, anti-halitosis agent, or a sleep apnea drug (e.g., Acetazolamide, medroxyprogesterone, fluoxetine, protriptyline, and dronabinol). In particular embodiments, when an array of sealed reservoir systems are employed, the therapeutic agent is released over time (e.g., into oral cavity) as various reservoirs and/or pre-sealed microchambers are un-sealed over time based on different thicknesses (or composition) of the liquid degradable membrane.

Figure 7:
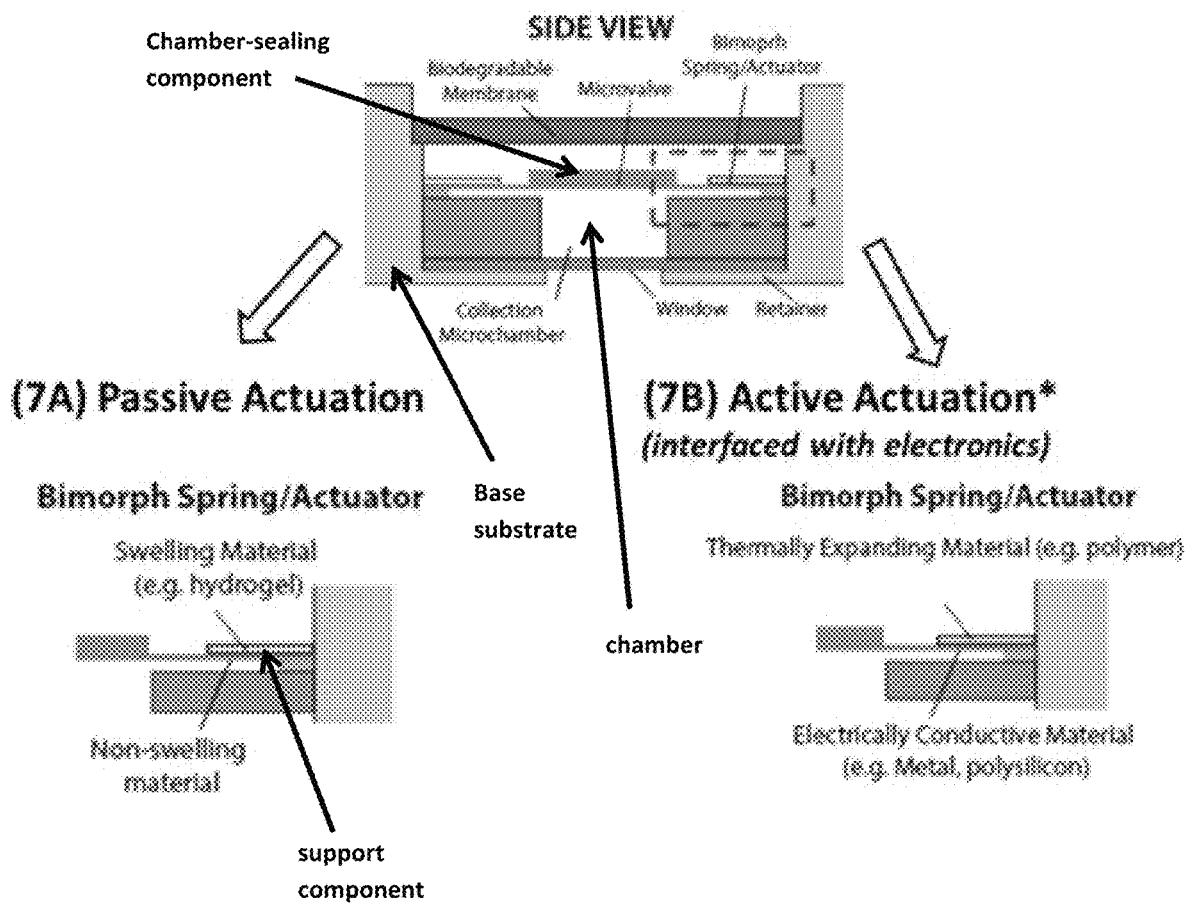
FIG. 7 shows (top) a reservoir with a microchamber therein.
Figure 8:
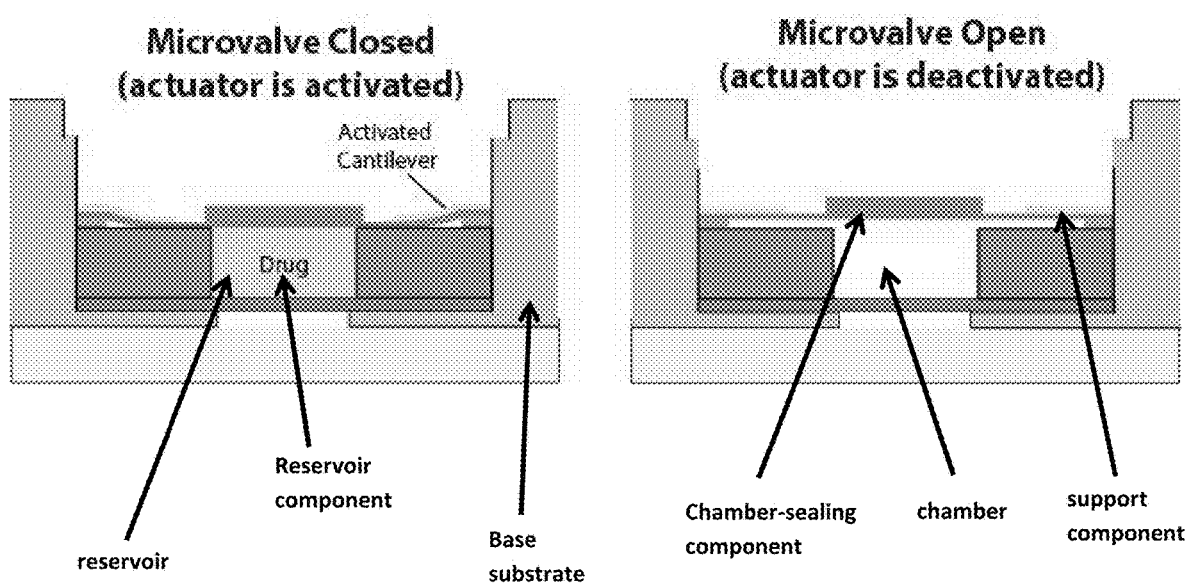
FIG. 8 shows an embodiment where an active valve is initially closed, and when it is activated (e.g., electrothermally), this causes the valve to open. When the valve is de-activated, it returns to its original position (open).
Figure 9:
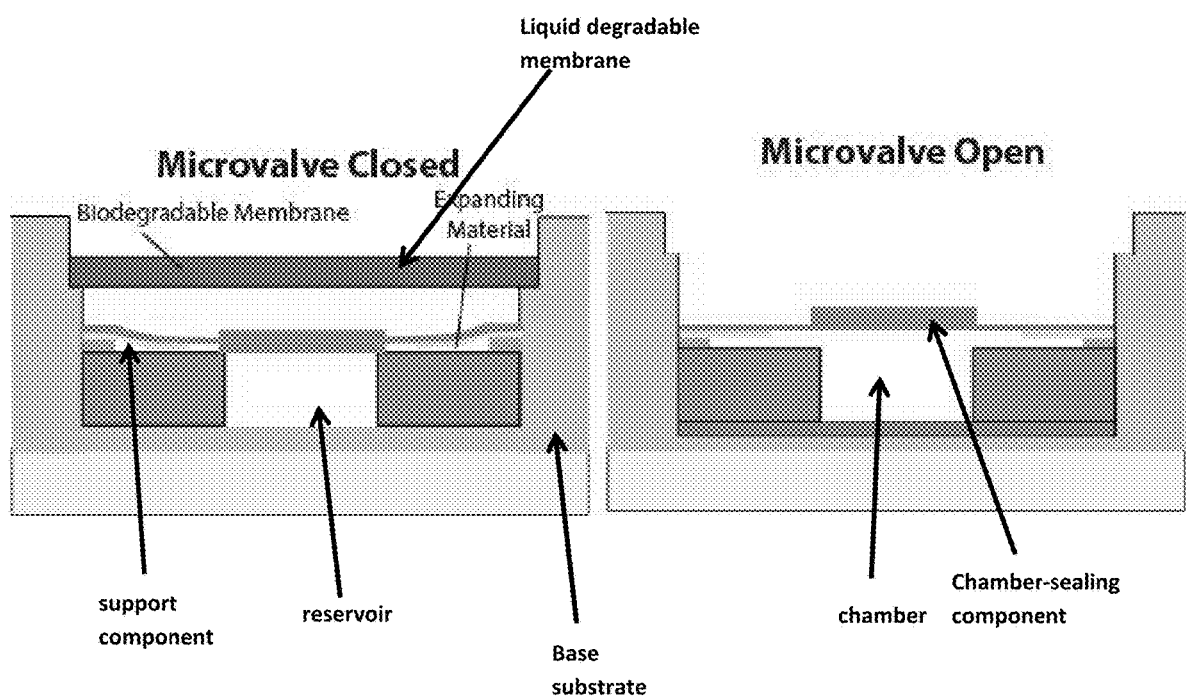
FIG. 9 shows an embodiment where a passive valve is initially closed, and when it is activated (e.g., by liquid, such as saliva), this causes the valve to open. The expanding material is below the non-expanding material, such that expansion of the expanding material causes the microchamber to be opened.
Figure 10A:
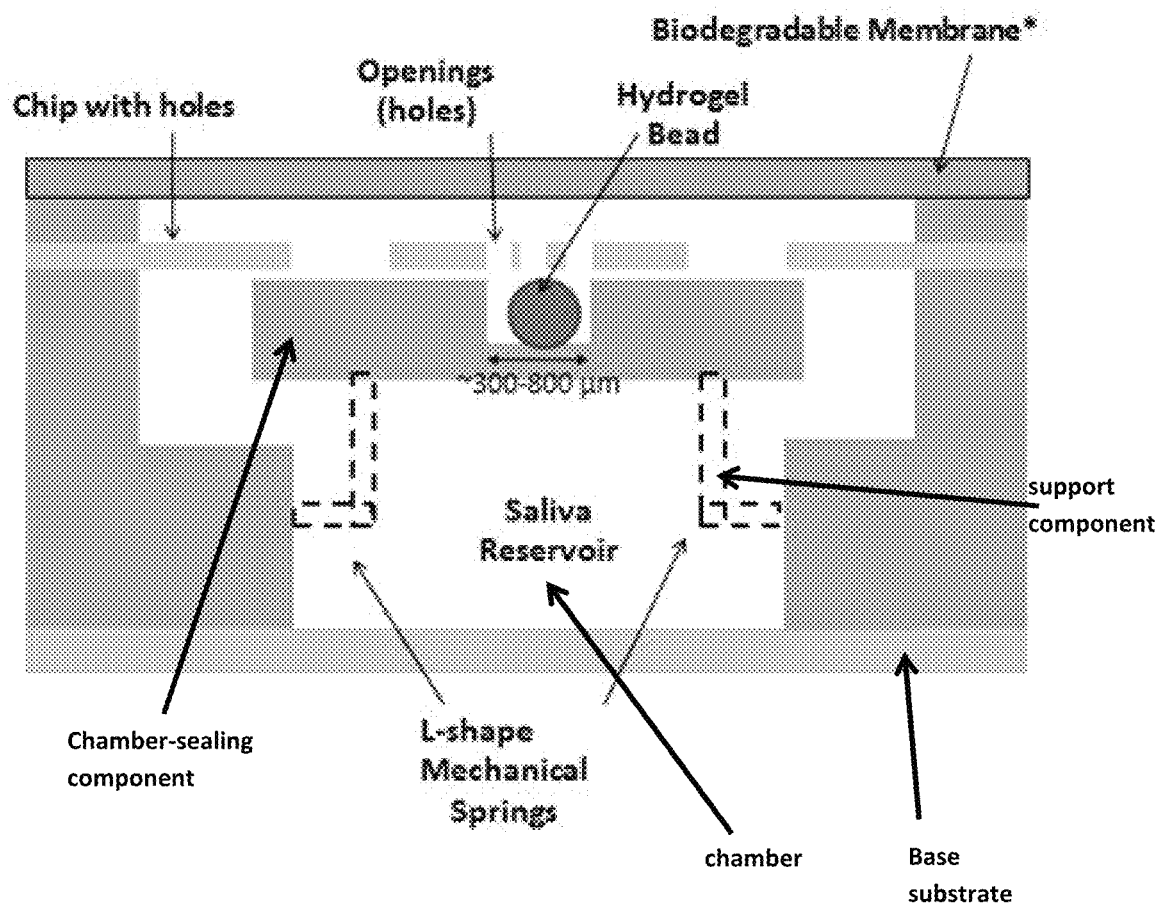
FIG. 10A shows a liquid collection device similar to FIG. 6, except it uses L-shaped springs to movable stage. In certain embodiments, two, three, four or more springs are used to support the stage.
Figure 10B:
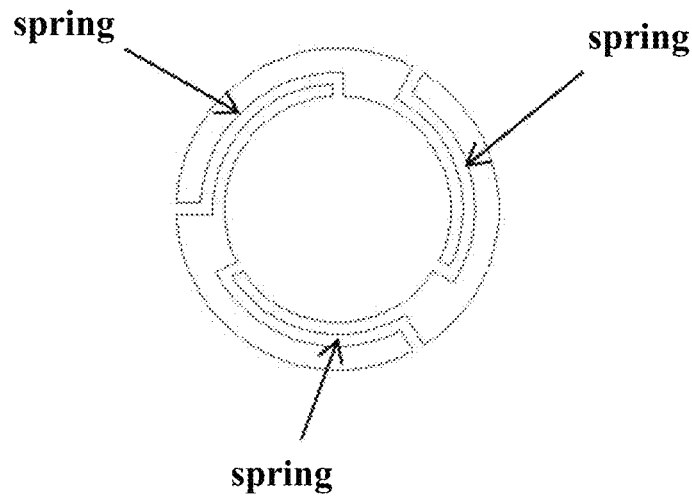
FIG. 10B shows an exemplary embodiment where three springs generally following the curvature of the round valve cap.

In certain embodiments, the reservoir component (e.g., sample detection component, sample collection component, or therapeutic agent), or other part of one or more of the systems herein (e.g., located in the reservoir), comprises an electronic component or electrically controlled component. In some embodiments, one or more electrical components from U.S. Pat. Pub. 2007/0106138 (herein incorporated by reference) is provided in the reservoir of a sealed reservoir component (e.g., a power source, control unit, processor, timing device, receiver, transceiver, battery, physiological sensor, transmitter, pH sensor, wires, etc.). In certain embodiments, the sealing or unsealing of the microchamber is controlled by electronics, thereby providing active control. One embodiment of such active control is provided in FIG. 7b, which shows a biomorph spring that can be actively activated by electronic control. Electrically conductive contact material causes the thermally expanding polymer (that is on top of the contact material) to swell, thereby pushing down and causing the microchamber to be sealed. This arrangement can be reversed with the conductive contact material on the top, where swelling of the thermally expanding polymer causes the microchamber to open. The thermally expanding material can be any suitable material that has a higher coefficient of thermal expansion than the contacting material. Examples of such materials include, for example, photoresists (e.g. SU8), polymers (e.g., parylene, polyimide, fluopolymers), elastomers (such as PDMS), aluminum, hydrogels, and M3 Crystal (3D printing material). In other embodiments, a piezoelectric material is used instead of the thermally expanding material. Examples of such materials include, for example, quartz single crystals, and piezoelectric ceramics, such as lithium niobate, gallium arsenide, zinc oxide, aluminium nitride and lead zirconate-titanate. In certain embodiments, rather than thermally expanding material, or piezoelectric material, the valves are activated electrostatically or electromagnetically. Examples of microvalves that can be used with the devices described herein are found in Au et al. Micromachines 2011, 2(2), 179-220 and Oh et al., Journal of Micromechanics and Microengineering, Volume 16, Number 5, March 2006; both of which are herein incorporated by reference in their entireties.

In certain embodiments, a sample collection component is employed inside the reservoir. In particular embodiments, the sample collection component comprises the chamber sealing systems described below. In other embodiments, the chamber sealing component is as described in U.S. Pat. Pub. 2007/0106138, which is herein incorporated by reference.

II. Chamber Sealing Systems

In certain embodiments, provided herein are chamber sealing systems. In certain embodiments, the chamber sealing systems comprise: a) a chamber, b) a chamber-sealing component, and c) at least one support component attached to said chamber-sealing component, wherein said at least one support components hold said chamber-sealing component at least partially away from said chamber such that said chamber is not sealed, wherein said at least one support component comprise liquid-activated material, and wherein said at least one support components is configured to change shape when contacted by a liquid causing said chamber-sealing component to seal said chamber. In particular embodiments, the chamber sealing system is attached to a base substrate, such as a mouth piece, with indentations created by individual teeth. In certain embodiments, the chamber sealing system is at the bottom of one of these indentations (see, e.g., FIG. 1). In other embodiments, the chamber sealing system is next to one of the indentations (e.g., part of a bump-out that does not line up with any teeth indentations).

In certain embodiments, the chamber (e.g., micro-chamber) has a shape selected from a square, well-shaped, a cone, or other shape. In certain embodiments, the chamber has a volume between 0.5 µl and 300 µl (e.g., 0.5 . . . 4 . . . 17 . . . 24 . . . 50 . . . 100 and 300 µl).

In some embodiments, the liquid activated material comprises a material selected from: hydrogel, sodium acrylic acid, acrylamide, and sodium acrylic acid/acrylamide copolymer. In certain embodiments, the liquid activated material comprises a water-swellable polymer. Water-swellable polymers, typically hydrogel-forming water-swellable polymers, also referred to as absorbent gelling material, AGM, or super-absorbent polymers, or SAP's. In certain embodiments, water-swellable polymers are made by initially polymerizing unsaturated carboxylic acids or derivatives thereof, such as acrylic acid, alkali metal (e.g., sodium and/or potassium) or ammonium salts of acrylic acid, alkyl acrylates, and the like in the presence of relatively small amounts of di- or poly-functional monomers such as N,N'-methylenebisacrylamide, trimethylolpropane triacrylate, ethylene glycol di(meth)acrylate, or triallylamine. The di- or poly-functional monomer materials serve to lightly cross-link the polymer chains thereby rendering them water-insoluble, yet water-swellable. These lightly crosslinked absorbent polymers contain a multiplicity of carboxylate groups attached to the polymer backbone. Further examples of water-swellable polymers include, but are not limited to, crosslinked polyacrylamide, crosslinked polyacrylate, crosslinked hydrolyzed polyacrylonitrile, salts of carboxyalkyl starch, salts of carboxymethyl starch, salts of carboxyalkyl cellulose, hydroxylethyl cellulose, salts of crosslinked carboxyalkyl polysaccharide, crosslinked copolymers of acrylamide and acrylate monomers, starch grafted with acrylonitrile and acrylate monomers, crosslinked polymers of two or more of allylsulfonates, 2-acrylamido-2-methyl-1-propane-sulfonic acid, 3-allyloxy-2-hydroxy-1-propane-sulfonic acid, acrylamide, acrylic acid monomers, and any combination thereof. Examples of commercially available water-swellable polymers include, but are not limited to, CRYSTALSEAL® (a water-swellable, synthetic polymer, available from Halliburton Energy Services, Inc.), DIAMOND SEAL@ (a water-swellable, synthetic polymer, available from Halliburton Energy Services, Inc.), and AD-200 (a water-swellable, synthetic polymer, available from Hychem, Inc.).

The one or more support components a not limited to a particular shape. In certain embodiments, a hydrogel sphere and one or more cantilevers, tabs, or arms, combine to form one or more support structures. In particular embodiments, cantilevers or other rigid or semi-rigid structures (e.g., tab, arm, etc.) are employed. In some embodiments, the cantilevers or other structures themselves are composed of liquid-activated material (e.g., when contacted with liquid, the cantilevers or other structures themselves swell such that they move and/or change shape). In other embodiments, the cantilevers or other structures are adjacent to the liquid-activated material such that they move and/or change shape upon contact with liquid. In certain embodiments, the cantilevers or other structures are 0.3 to 15 mm in length and/or width (e.g., 0.3 . . . 1.0 . . . 5 . . . 10 . . . or 15 mm in length and/or width). In particular embodiments, the cantilevers or other structures are 0.05 mm to 4 mm in depth (e.g., 0.05 . . . 0.1 . . . 1.0 . . . 4 mm in depth).

In certain embodiments, the chamber sealing component has a shape selected from circular, oval, square hexagonal, or other shape. In certain embodiments, the chamber sealing component comprises a diaphragm or other membrane. In particular embodiments, the chamber sealing component is rigid, semi-rigid, or flexible. In certain embodiments, the chamber sealing component is 0.3 to 15 mm in length and/or width and/or diameter (e.g., 0.3 . . . 1.0 . . . 5 . . . 10 . . . or 15 mm in length and/or width). In particular embodiments, the chamber sealing component is 0.05 mm to 4 mm in depth (e.g., 0.05 . . . 0.1 . . . 1.0 . . . 4 mm in depth).

III. Micro-Reservoir Units

Figure 1:
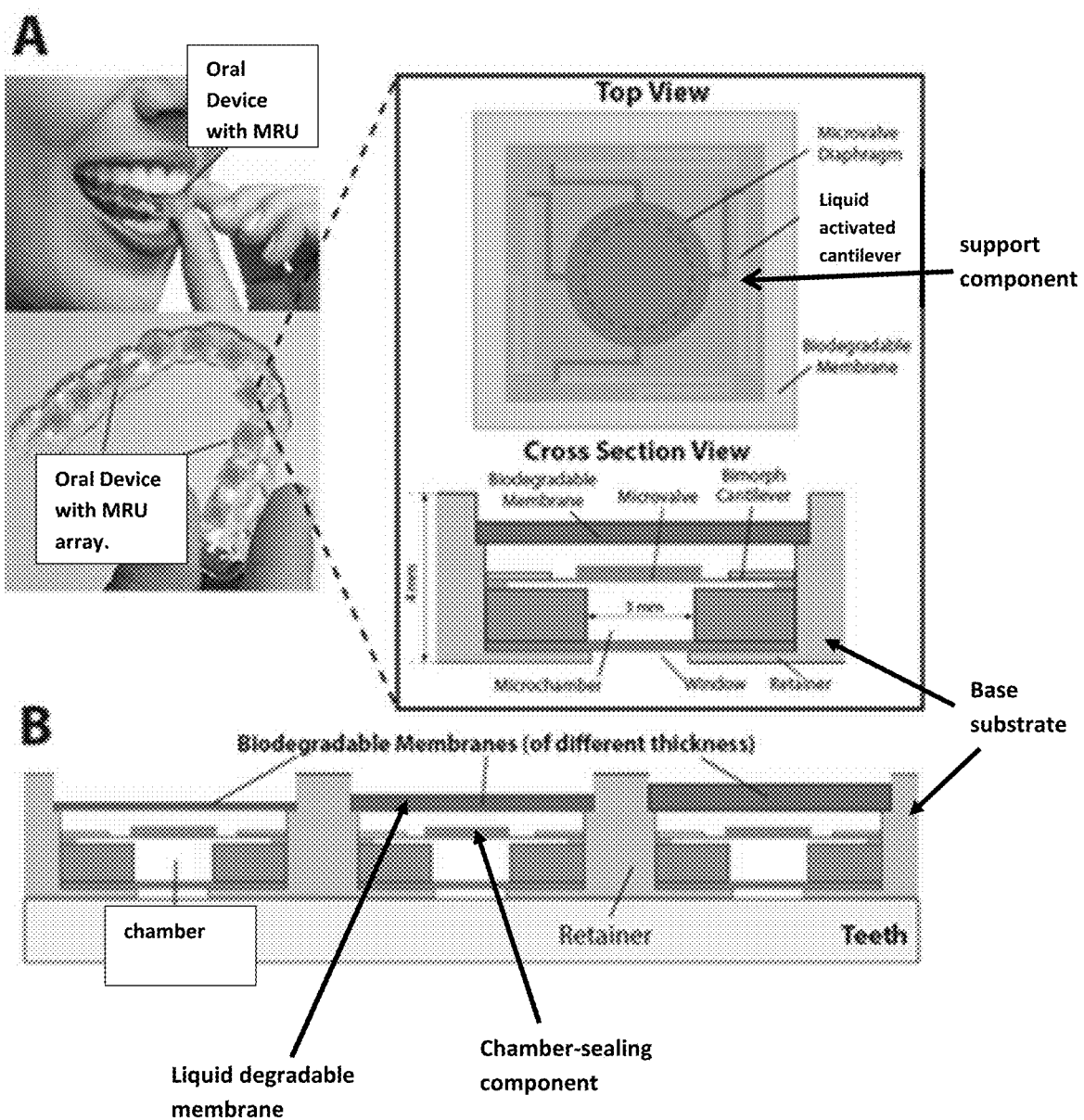
FIG. 1, panel A, right side, shows a chamber sealing system (CSS) and a sealed reservoir system (SRS) combined together in a single micro-reservoir unit (MRU), where the CSS is initially sealed inside the SRS.

In certain embodiments, the chamber sealing system (CSS) and sealed reservoir systems (SRS) are combined together in a single micro-reservoir unit (MRU), where the CSS is initially sealed inside the SRS (see, e.g., FIG. 1 and FIG. 5). In particular embodiments, the MRU is attached to a base substrate, such as a mouth piece, with indentations created by individual teeth. In certain embodiments, the MRU is at the bottom of one of these indentations (see, e.g., FIG. 1). In other embodiments, the MRU is next to one of the indentations (e.g., part of a bump-out that does not line up with any teeth indentations).

A plurality of the MRUs may be attached to or integral with a base substrate (e.g., mouthpiece or water sampling device) such that an array of MRUs are present in a single liquid activated device. FIG. 1A, right side, provides an example of a single MRU. FIG. 1A, left side, shows a plurality of MRUs (a MRU array) attached to a mouthpiece base substrate. In such embodiments, the liquid that degrades the liquid degradable membrane is saliva. Saliva is also the liquid that activates the liquid-activated material in the four support components (cantilevers composed of, or adjacent to, hydrogel material) shown in FIG. 1. FIG. 1B also shows an array of MRUs with three separate MRUs In certain embodiments, the liquid activated devices herein are composed of an array of MRUs that is integrated into a 3D printed retainer for subject (e.g., resembling a teeth whitening retainer) or in another base substrate, such as a water-testing device or other intra-oral device. An example of how such a liquid activated device may be employed for saliva collection is as follows. The liquid activated device with MRU array is placed in the mouth of a patient for a certain period of time (e.g., 1 hour . . . 12 hours . . . 24 hours . . . 48 hours . . . etc.) and collects a small amount of saliva in a chamber every 30 minutes or 1 hour or other time period. At the end of the monitoring period, the liquid activated device is removed from the mouth, and the saliva samples are recovered (or observed through a window in the bottom of each chamber) from each MRU (e.g., in the chamber, which is now sealed) and analyzed using laboratory protocols and equipment. In operation, when saliva contacts the biodegradable membrane covering each sealed reservoir system, it degrades the membrane, eventually allowing saliva to enter the reservoir. Inside the reservoir, the saliva contacts the support components, causing them to change shape and cause the chamber-sealing component to seal the chamber, after an amount of saliva has entered the chamber and been trapped therein. In certain embodiments, a window forms at least the bottom of the chamber, which can be pierced to collect saliva. Alternatively, the window can be used to observe the saliva and any reagents that have mixed therewith to provide a detectable signal. In certain embodiments, the collection time point for the MRU array, is controlled through the thickness of the biodegradable membrane (e.g., thicker membranes allow a particular MRU to be activated later in time than MRUs with thinner membranes), and/or is controlled based on the use of different materials that degrade at different rates. This can be seen in FIG. 1B, which shows thinner degradable membrane on the left most MRU, a thicker degradable membrane in the middle MRU, and an even thick degradable membrane on the right most MRU.

Figure 2:
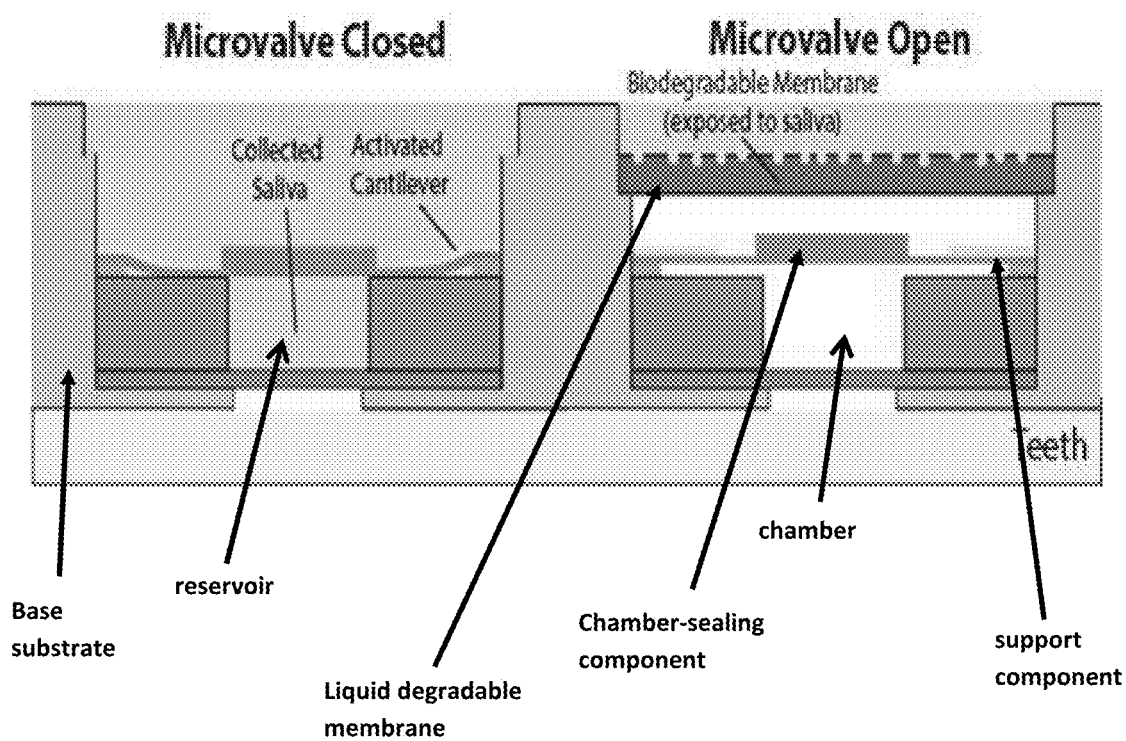
FIG. 2, on the right side, show an MRU with the biodegradable membrane just beginning to degrade, but still intact. The chamber sealing system inside the reservoir has not yet been exposed to liquid (e.g., saliva), so micro-valve is still open (the support components have not yet changed shape, so they hold the chamber-sealing component away from the micro-chamber below. The left side of FIG. 2 shows the micro-valve closed after being exposed to saliva. The support components (cantilevers) have changed shape in response to the saliva and pushed the chamber-sealing component (e.g., diaphragm in this figure) down, sealing the micro-chamber with some saliva trapped therein.

FIG. 2, on the right side, show an MRU with the biodegradable membrane just beginning to degrade, but still intact. The chamber sealing system inside the reservoir has not yet been exposed to liquid (e.g., saliva, water, etc.), so micro-valve is still open (the support components have not yet changed shape, so they hold the chamber-sealing component away from the micro-chamber below. The left side of FIG. 2 shows the micro-valve closed after being exposed to saliva. The support components (e.g., cantilevers) have changed shape in response to the saliva and pushed the chamber-sealing component (e.g., diaphragm in this figure) down, sealing the micro-chamber with some saliva trapped therein. This stores the saliva until it can be retrieved and analyzed, or analyzed in place.

As shown in the exemplary embodiments in FIG. 2, chamber sealing component is a exemplified as a circular rigid flap that is connected to four support components (bimorph cantilevers are exemplified). Each cantilever act as a mechanical spring and it is made out of two layers (polysilicon (poly-Si) and hydrogel). In this exemplary embodiment, the chamber-sealing component is initially open, as the difference in the residual stress between the two layers result in out of plane bending of the support components (e.g., the cantilevers). When the membrane dissolves, the cantilever is exposed to water (saliva contains 99.5% water), the hydrogel swells and bends the cantilever downward closing the flap of the chamber sealing component (e.g., diaphragm) and therefore, sealing the saliva-filled, micro-chamber in seconds.

As shown in FIG. 2, each micro-reservoir unit (MRU) in the array includes 3 components: (1) a biodegradable membrane that dissolves in liquid, such as saliva, or water; (2) a micro-chamber that can store captured liquid (e.g., 1-50 µl of saliva), and (3) a liquid-activated microvalve composed of a chamber-sealing component (e.g., diaphragm) and support components (e.g., cantilevers) composed in part of liquid-activated material (e.g., hydrogel).

The general operation of an MRU is straightforward, making its operation robust and reliable. For example, when a base substrate with one or more MRUs is placed in the mouth, saliva comes in contact with the biodegradable membrane(s) and starts dissolving it. After the membrane has dissolved enough to allow liquid to pass through into the reservoir, saliva fills the micro-chamber and the saliva-activated valve closes in seconds (e.g., cantilevers change shape, causing the diaphragm to close down over the micro-chamber). The time point at which each microvalve closes is controlled through the thickness, and/or composition, of the biodegradable membrane. The thicker membranes need longer time to dissolve versus thin ones. Therefore, each microvalve is activated at a specific time point that is defined by the thickness of its membrane. This mechanism allows sequential activation of the microvalves, allowing liquid samples to be collected at specific time points when an array of MRUs is employed.

In certain embodiments, one or more features of MRU's include, for example: (1) zero power requirements and no need for electronics, (2) modular integration of an intra-oral device (e.g., teeth retainer) with a MRU array (e.g., allowing a custom-fit to any patient), (3) MRU microfabrication in a batch manufacturing, high resolution process, that leads to low cost and robust device operation, (4) design versatility that allows MRUs to be easily modified to collect liquid (e.g., saliva) samples at any time point and serial time points, (5) Scalability: the miniature size of the MRU arrays, allows the integration of tens or hundreds MRUs into a base substrate (e.g., teeth retainer or water sampling device) enabling longer, multi-point, monitoring periods.

In certain embodiments, a liquid activated device herein composed of an intra-oral device (e.g., mouthpiece) with an array of MRUs is employed to study sleep disorders by collecting saliva samples periodically during sleep of a subject. For example, such liquid activated devices are employed to study the relationship between changes in the circadian clock and sleep disorders at home. Use of such liquid activated devices could change the way physicians diagnose and treat sleep related diseases. It has been shows that the salivary gland clock works at least partially independently of the master brain clock to regulate salivary flow. Over-night monitoring of DLMO with the liquid activated devices herein will help to understand how inputs that control the biological clock mechanisms in our bodies function. Such information will enhance efficacy of drugs, such as Tasimelteon that resets the circadian clock maximizing its effects by adapting treatment time to each patient's own circadian bio-rhythms.

Circadian clock disruption can be detected by measuring saliva biomarkers such as melatonin and other others. Such disruptions have been directly implicated in almost all human diseases including cancer, autoimmune, diabetes, cardiovascular, metabolic syndrome, etc. Saliva biomarkers could also be detected in animals (e.g., dogs, cats, cattle, pigs, horses, etc.). As such, in some embodiments, the devices and systems described herein are used to measure circadian clock disruptions by measuring one or more biomarkers in the saliva of a subject (e.g., as an aid to treat a disease such as cancer, autoimmune disease, diabetes, cardiovascular, metabolic syndrome, etc.).

In certain embodiments, the MRUs and MRU arrays herein allow health care workers to obtain a complete profile of saliva diagnostic markers for patients, eliminating contradictory results due to circadian regulation of the majority of saliva proteins. In some embodiments, the MRUs and MRU arrays include a colorimetric assay (or other types of assays) adapted to each microchamber that can detect in real time the levels of a given saliva biomarker.

EXAMPLES

The following examples are for purposes of illustration only and are not intended to limit the scope of the claims.

Example 1

3D Printed Prototype and Sleep Study Work

Work was conducted to design and fabricate a proof of-concept prototype, and is shown in FIG. 3. The prototype is composed of a 3D printed saliva collection container, made out of a biocompatible material (M3 Crystal). A biodegradable membrane was not included in the prototype, as the goal was to demonstrate the operation principle of the valve. The container integrated a 10 mm in diameter, 10 mm thick collection well (1.8 ml total volume) with a water-activated valve. The valve has a 15 mm in diameter diaphragm that is suspended over the collection well through 4 cantilevers. A hydrogel sphere (made of sodium acrylic acid/acrylamide copolymer) is mounted in a top of each cantilever and enclosed by a small cubic chamber that has small openings on its side to allow the hydrogel to get exposed to saliva. The valve is initially open. When the valve comes in contact with saliva, the hydrogel sphere swells, bending the cantilever beams downward. As a result the diaphragm seals the chamber that has been filled with saliva. An experiment was performed with water and resulted in exceptional performance. The hydrogel-activated valve created a good seal in only ~30 sec while the chamber was completely filled the water. No leakage was observed even after several hours.

Melatonin Detection in Saliva.

Figure 4:
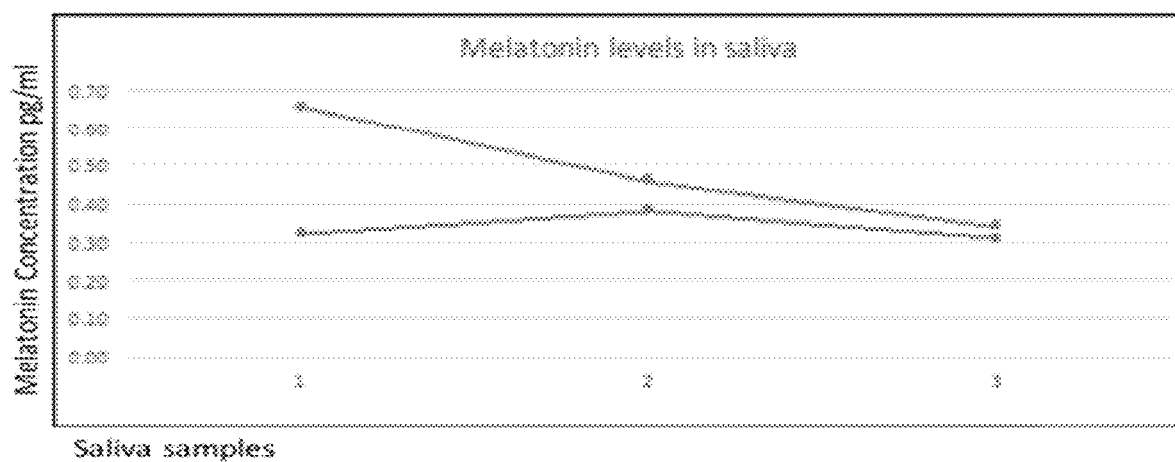
FIG. 4 shows results from Example 1, wherein melatonin was detected above the standard detection levels (25 pg/ml) using 100, 50, and 10 µl of saliva. Standard detection levels are without variations using melatonin antibody as positive control.

Work was conducted, testing different concentrations of saliva to define the approximate minimum amount of saliva needed to accurately assess melatonin (FIG. 4). Based on the assays employed for this particular work, the data shows that melatonin can be accurately detected in a minimum 10 µl of saliva.

Circadian Rhythm Assessment in Sleep Clinic.

Endogenous circadian rhythm profile is characterized following standardized procedures. Briefly, saliva samples are collected every 60 minutes using Salivettes (Sarstedt, Newton, NC) across one 24-hour period (24 samples total) in dim light conditions (<30 lux) beginning 6 hours prior to habitual bedtime. Samples are collected from participants seated for at least 10 minutes after rinsing their mouth and brushing their teeth without toothpaste if drinks or snacks were consumed. During the assessment, subjects are monitored to ensure wakefulness, engage in quiet activities, and be provided with caffeine-free snacks and fluid. Nonsteroidal anti-inflammatory agents are not permitted within 72 hours of testing because they have been shown to suppress melatonin. Alcohol and caffeine are also restricted. The resulting samples are centrifuged for two minutes, frozen (−20° C.), and are assayed using Bühlmann Laboratory (ALPCO Diagnostics, Salem, NH).

Primary outcomes include the peak value for melatonin (MLT), area under the curve (AUC) using the trapezoidal method, and dim light melatonin onset (DLMO, see FIG. 5) and dim light melatonin offset (DLMOff). For each melatonin profile, a threshold is calculated as the mean of the three low consecutive daytime values plus twice the standard deviation of these points. DLMO is calculated as the point when the melatonin concentration exceeds and remains above this threshold for at least one hour. DLMOff are defined as the point when melatonin levels fall below and remain below this threshold for 1 hour.

Example 2

Intra-Oral Device with MRU Arrays

A 24 unit MRU array may be fabricated in a dental retainer, thereby allowing sample collection patients wearing the retainer for 24 hours.

The Teeth Retainer.

The teeth retainers can made out of Visijet M3 Dentcast and be 3D printed at a 3D Lab after intraoral 3D teeth scans of each patient. Other suitable acrylic or suitable materials may be employed as well. The retainer could also be made using dental impressions. VisijetM3 Dentcast is a biocompatible, durable acrylic resin that 'produces high-quality, smooth surface crowns, copings and other related dental prosthesis and restorations.' The retainer have openings on its inner side so it can accommodate the 24 units of the MRU array. Other sides could be used, allowing for not only single biomarker analysis, but also, for example, omics applications such as microbiomics, circadiomic, metabolmics, genomics, etc.

The Saliva Collection MRU Array.

Each sealed reservoir system in the MRU array can have a footprint of 5 mm×5 mm and a depth of 2 mm and accommodate a chamber sealing system with a 3 mm in diameter saliva collection microchamber (FIG. 5). Each microchamber collects ~15 µl of saliva and it is tight-sealed by a polysilicon microvalve. The bottom of the microchamber is covered with an elastomer (PDMS) that may be pierced with a needle at the completion of each experiment/study in order to retrieve the collected saliva samples. The MRU array is fabricated using standard micromachining processes. Starting with a silicon (Si) wafer, one can deposit and pattern layers of Sift, polysilicon (poly-Si), and hydrogel to create the microvalve cantilevers/diaphragm. Lastly, one can perform a Deep Reactive Ion Etching (DRIE) step to open the back side of the wafer. For the cantilevers, a photopatternable hydrogel (PEGDA-DMPA) is employed that is spin cast on top of the poly-Si cantilevers. The PEGDA-DMPA hydrogel comprises of poly(ethylene glycol)diacrylate (PEGDA) and a photoinitiator, (2,2'-dimethoxy-2-phenylaxetophenone) (DMPA) and it is patterned using standard photolithographic techniques. All material used in microfabrication process have been reported to be biocompatible.

The operation of the micro-reservoir employs two important parameters: (i) the activation time point of the microvalve which is determined by the thickness of the biodegradable membrane, and (ii) the leakage rate of the microvalve which is determined by the stiffness (elastic modulus and dimensions) of the microvalve cantilevers that act as mechanical springs. To quantify those 2 parameters, one can fabricate biodegradable membranes of 15, 30, 45, . . . , up to 375 µm thick. The biodegradable membrane is a mixture of poly(ethyleneglycol) (PEG) and polyanhydride and is synthesized using standard protocols. Then, the polymer solution is spin cast on a bare wafer to the desired thickness and dried. The membranes are then be diced and glued on top of the 3D printed retainer using a dental adhesive. Polyanhydrides are biocompatible, biodegradable polymers and widely used for sustained drug delivery applications.

PEG is used to increase the degradation time of the membrane. Studies indicate a degradation rate of ~15 µm/hour, therefore the 15, 30, . . . 375 µm thick membranes will degrade completely in 1, 2, . . . 24 hours. One can immerse each membrane in artificial saliva and monitor under a microscope the time needed for each membrane to dissolve (to thus obtain the membrane degradation rate (DR)). It is also possible that a small amount of saliva will diffuse through the membrane while biodegradation takes place. One can attach the membranes in micro-reservoirs (with no valves) and measure how much saliva is collected in the reservoirs over time. One can fabricate microvalves with different spring stiffness's. One can vary the thickness of the hydrogel/silicon cantilevers (e.g., 1-4 µm) as well as the thickness of the hydrogel layer (e.g., 5-20 µm). The dimensions of the beams affect the force that is required to close each microvalve and therefore will affect the leakage. The leakage rate can be measured as follows: fill the micro-chambers (no membranes used in this experiment) with known concentration of melatonin (~2.5-25pg/ml) diluted in artificial saliva. After the microvalves are activated sealing the micro-chamber, one can pipette a buffer solution on top of the valves. After 24 hours, one can remove the buffer solution and measure the concentration of the melatonin in the micro-chambers. By quantifying the change in melatonin, one can obtain the leakage rate.

The Integrated MRU ARRAY.

After obtaining the degradation rate and an optimum spring thickness for minimum leakage rate, one can fabricate a micro-array with 24 MRUs, with each reservoir being activated every 1 hour. That can be achieved by adjusting the thickness the other membrane in each micro-reservoir as described above. The MRU array and with membranes can be manually assembled and glued into the 24 wells of the retainer using a dental adhesive. The integrated MRU array can be placed in a small bath containing artificial saliva with no melatonin. One can replace the artificial saliva solution with a fresh one containing incrementally higher melatonin concentrations every hour ($1^{st}$ hr: 2.5pg/ml of melatonin, $24^{th}$ hr: 25pg/m of melatonin). After 24 hours, one can analyze the sample collected in the array and compare the concentration of the melatonin in the MRU array with the known melatonin concentration of the artificial saliva solutions.

Microvalve Leakage Rate.

For each value of the cantilever stiffness (defined by the thickness of the silicon/hydrogel bimorph) one will obtain the leakage rate in µl/day. Stiffer beams are less fragile and, in general, it is expected that they will provide a tight seal compared to more flexible beams. One can create a plot depicting the dependence of cantilever stiffness versus leakage rate. In general, the optimum spring dimensions will be the ones providing minimum leakage. A<5% leakage rate (corresponding to 1 µl/24 hr) is generally acceptable.

Degradation Rate (DR) of the Biodegradable Membrane.

Preliminary data by others indicates that a thickness of 15 µm will fully dissolve in ~1 hour. By monitoring the membrane degradation process, one will obtain the membrane DR (in microns/h). The obtained DR value is used to select the optimum membrane thicknesses in the integrated MRU array. One can repeat those experiments with saliva solutions at different pH to find that dependence of pH on DR. A<5% change on the DR for pH values within the physiological range (5.6-7.9) will be generally acceptable.

Accuracy and Precision Error.

As described above, one can collect artificial saliva samples of known melatonin concentration from the MRU array for a period of 24 hours. The measured melatonin concentration from each micro-reservoir is compared to the known melatonin concentration in order to quantify the accuracy error. The above experiments are repeated 10-15 times to obtain the precision error. An accuracy and precision error of <5% is acceptable.

Clinical Validation of MRU Array:

Circadian Rhythm assessment (DLMO) is a key diagnostic tool for patients with sleep disorders and co-morbidities. This assessment tool requires 24 hours stay in a specialized Sleep Clinic and saliva collection by spitting every 30-60 min. Limitations of this include patience compliance, cost, access to specialized centers, etc., all of which prevent the use of DLMO for diagnosis of sleep disorders. The MRU array overcomes those limitations.

Experimental Protocol.

Participants (n=20) may be healthy individuals equally distributed in two groups and recruited from the dental clinics. In a first protocol, participants (n=10) will complete a circadian phase assessment using the MRU array intra-oral device, followed by a sleep laboratory circadian phase assessment a week later. In a second Protocol, participants will complete a sleep laboratory phase assessment first, followed by a phase assessment the using MRU array intra-oral device a week later.

Inclusion and Exclusion Criteria:

Based on their responses to screening questionnaires, all participants will be healthy individuals without history of medical conditions, psychiatric symptoms of personality or depression or sleep disorders (Pittsburgh Sleep Quality Index, Insomnia Severity Index, Berlin Sleep Apnea Questionnaire, International Restless Legs Syndrome Study Group consensus criteria for restless leg syndrome). All night shifts workers are excluded. All participants should be medication free because they can suppress melatonin, consume only moderate caffeine (<300 mg/day) and alcohol (<2 drinks/day), and have a BMI between 18.5-29.8 kg/m². All participants will provide written informed consent.

Although only a few exemplary embodiments have been described in detail, those skilled in the art will readily appreciate that many modifications are possible in the exemplary embodiments without materially departing from the novel teachings and advantages of this disclosure. Accordingly, all such modifications and alternative are intended to be included within the scope of the invention as defined in the following claims. Those skilled in the art should also realize that such modifications and equivalent constructions or methods do not depart from the spirit and scope of the present disclosure, and that they may make various changes, substitutions, and alterations herein without departing from the spirit and scope of the present disclosure.

We claim:

1. An oral device comprising:
   a) a base substrate comprising an intra-oral device selected from a group consisting of: a mouthpiece, a retainer, an oral appliance, and an oral orthotic, and
   b) a micro-reservoir unit (MRU) attached to, or integral with, said base substrate, wherein said MRU comprises a chamber sealing system that is inside a sealed reservoir system,
      i) wherein said chamber sealing system comprises:
         A) a chamber,
         B) a chamber-sealing component, and
         C) at least one support component attached to said chamber-sealing component, wherein said at least one support component: i) holds said chamber-sealing component at least partially away from said chamber such that said chamber is not sealed, or ii) holds said chamber-sealing component against said chamber such that said chamber is sealed,
         wherein said at least one support component comprises thermally expanding material and electrically conductive material, and
         wherein said at least one support component is configured to change shape when activated by electrical current causing: i) said chamber-sealing component to seal said chamber if initially not sealed, or ii) said chamber-sealing component to un-seal said chamber if initially sealed; and ii) wherein said sealed reservoir system comprises:
  A) a reservoir,
  B) at least one reservoir component inside said reservoir, wherein said reservoir component is selected from the group consisting of: a sample detection component, a sample collection component, and a therapeutic agent component, and
  C) a liquid degradable membrane stretching across said reservoir such that said at least one reservoir component is sealed inside said reservoir.

2. The device of claim 1, wherein said thermally expanding material comprises a thermally expanding polymer.

3. The device of claim 1, wherein said electrically conductive material is configured to heat up when electrical current passes therethrough.

4. The device of claim 1, wherein said intra-oral device comprises said mouthpiece.

5. The device of claim 1, wherein said intra-oral device comprises said retainer.

6. The device of claim 1, wherein said intra-oral device comprises said oral appliance.

7. The device of claim 1, wherein said intra-oral device comprises said oral orthotic.

8. The device of claim 1, wherein said at least one support comprises at least one cantilever.

9. The device of claim 1, wherein said at least one support comprises at least two cantilevers.

10. The device of claim 1, wherein said at least one support comprises at least one biomorph spring.

11. The device of claim 1, wherein said reservoir component comprises said sample detection component.

12. The device of claim 11, wherein said sample detection component comprises an analyte binding component.

13. The device of claim 12, wherein said analyte binding component is selected from the group consisting of: an anti-analyte antibody or analyte binding portion thereof, a nucleic acid sequence configured to hybridize to the analyte, a small molecule configured to bind to the analyte, and a receptor for the analyte.

14. The device of claim 12, wherein said analyte binding component comprises an aptamer for said analyte.

15. The device of claim 10, wherein said sample detection component comprises melatonin detection reagents.

16. The device of claim 1, wherein said sealed reservoir system further comprises a battery.

17. The device of claim 1, wherein said chamber has a liquid volume of between 1 and 75 pl, and/or wherein said reservoir has a liquid volume of between 20 pl and 600 pl.

18. The device of claim 1, wherein said chamber-sealing component comprises a diaphragm, film, or plastic fitted cover.

* * * * *